(12) United States Patent
Friedman et al.

(10) Patent No.: US 11,841,338 B2
(45) Date of Patent: Dec. 12, 2023

(54) 2H TO 1T PHASE BASED TRANSITION METAL DICHALCOGENIDE SENSOR FOR OPTICAL AND ELECTRONIC DETECTION OF STRONG ELECTRON DONOR CHEMICAL VAPORS

(71) Applicant: The Government of the United States of America, as Represented by the Secretary of the Navy, Arlington, VA (US)

(72) Inventors: Adam L. Friedman, Silver Spring, MD (US); F. Keith Perkins, Alexandria, VA (US); James C. Culbertson, Alexandria, VA (US); Aubrey T. Hanbicki, Washington, DC (US); Paul M. Campbell, Alexandria, VA (US)

(73) Assignee: The Government of the United States of America, as represented by the Secretary of the Navy, Arlington, VA (US)

( * ) Notice: Subject to any disclaimer, the term of this patent is extended or adjusted under 35 U.S.C. 154(b) by 393 days.

(21) Appl. No.: 17/032,658

(22) Filed: Sep. 25, 2020

(65) Prior Publication Data

US 2021/0080419 A1 Mar. 18, 2021

Related U.S. Application Data

(60) Division of application No. 15/652,491, filed on Jul. 18, 2017, now Pat. No. 10,801,987, which is a
(Continued)

(51) Int. Cl.
*G01N 27/26* (2006.01)
*G01N 27/12* (2006.01)
(Continued)

(52) U.S. Cl.
CPC ............. *G01N 27/26* (2013.01); *C01B 19/04* (2013.01); *C01G 33/00* (2013.01); *C01G 35/00* (2013.01);
(Continued)

(58) Field of Classification Search
CPC ........ G01N 27/26; G01N 21/65; G01N 21/77; G01N 27/125; C01B 19/04; C01G 33/00;
(Continued)

(56) References Cited

U.S. PATENT DOCUMENTS 5,129,262 A * 7/1992 White .................... G01P 15/08
310/313 R
2009/0218235 A1* 9/2009 McDonald ........... G01N 27/127
204/431
(Continued)

OTHER PUBLICATIONS

Dynamics of chemical vapor sensing with MoS2 using 1T/2H phase contacts/channel. Adam L. Friedman, F. Keith Perkins, Aubrey T. Hanbicki, James C. Culbertson, Paul M. Campbell Nanoscale, 2016, 8, 11445-11453 (Year: 2016).*

*Primary Examiner* — Brian R Gordon
*Assistant Examiner* — Dwan A Gerido
(74) *Attorney, Agent, or Firm* — US Naval Research Laboratory; Rebecca L. Forman

(57) ABSTRACT

Optical and electronic detection of chemicals, and particularly strong electron-donors, by 2H to 1T phase-based transition metal dichalcogenide (TMD) films, detection apparatus incorporating the TMD films, methods for forming the detection apparatus, and detection systems and methods based on the TMD films are provided. The detection apparatus includes a 2H phase TMD film that transitions to the 1T phase under exposure to strong electron donors. After exposure, the phase state can be determined to assess whether all or a portion of the TMD has undergone a transition from the 2H phase to the 1T phase. Following
(Continued)

detection, TMD films in the 1T phase can be converted back to the 2H phase, resulting in a reusable chemical sensor that is selective for strong electron donors.

8 Claims, 11 Drawing Sheets

Related U.S. Application Data continuation-in-part of application No. 62/363,882, filed on Jul. 19, 2016.

(51) Int. Cl.
| | |
|---|---|
| G01N 21/77 | (2006.01) |
| G01N 21/65 | (2006.01) |
| C01B 19/04 | (2006.01) |
| C01G 33/00 | (2006.01) |
| C01G 35/00 | (2006.01) |
| C01G 39/06 | (2006.01) |
| C01G 41/00 | (2006.01) |
| C07C 211/05 | (2006.01) |
| C07C 211/00 | (2006.01) |
| C07C 211/07 | (2006.01) |
| G01N 21/78 | (2006.01) |
| C12N 9/16 | (2006.01) |
| G01N 21/64 | (2006.01) |
| H04B 7/00 | (2006.01) |

(52) U.S. Cl.
CPC ............ *C01G 39/06* (2013.01); *C01G 41/00* (2013.01); *C07C 211/05* (2013.01); *C07C 211/07* (2013.01); *G01N 21/65* (2013.01); *G01N 21/77* (2013.01); *G01N 27/125* (2013.01); *C12N 9/16* (2013.01); *G01N 21/64* (2013.01); *G01N 21/783* (2013.01); *H04B 7/00* (2013.01)

(58) Field of Classification Search
CPC ........ C01G 35/00; C01G 39/06; C01G 41/00; C07C 211/05; C07C 211/07
See application file for complete search history.

(56) References Cited

U.S. PATENT DOCUMENTS

2012/0270205 A1* 10/2012 Patel .................... G01N 27/021
 435/287.7
2017/0073809 A1* 3/2017 Choi .................. C23C 14/0021

* cited by examiner

FIGURE 4A
FIGURE 4B
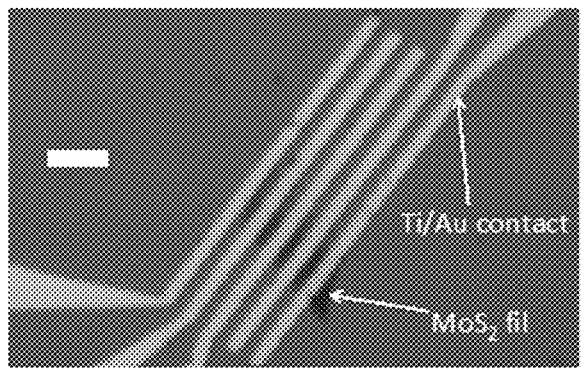
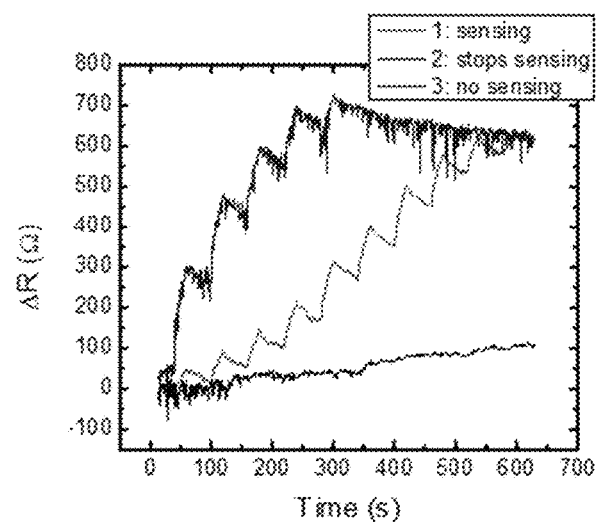

FIGURE 5A
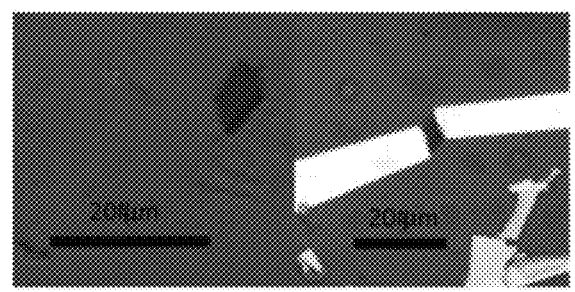
FIGURE 5B
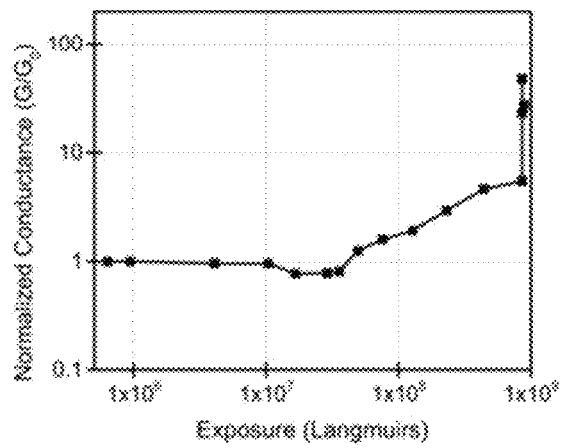
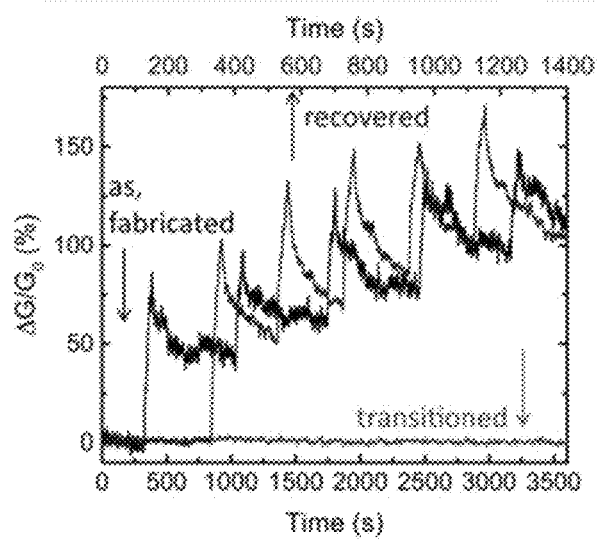
FIGURE 5C
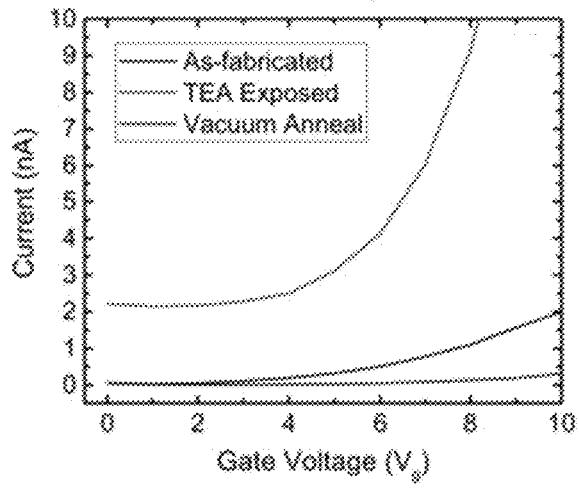
FIGURE 5D

FIGURE 6A
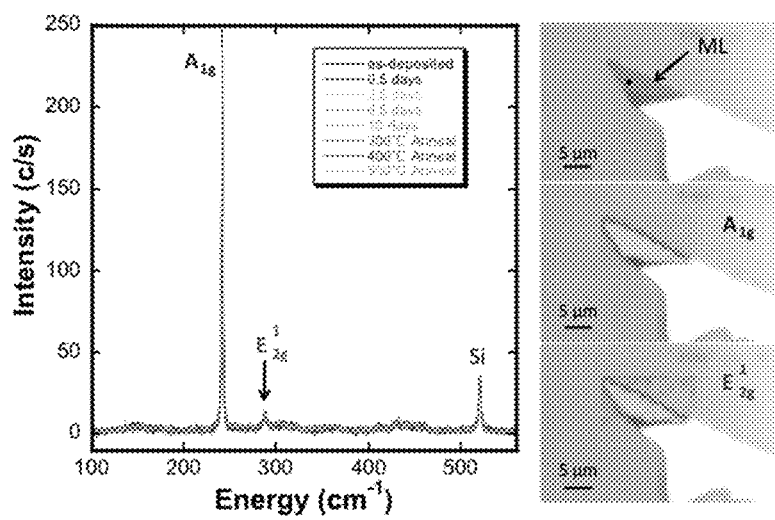
FIGURE 6B
FIGURE 6C
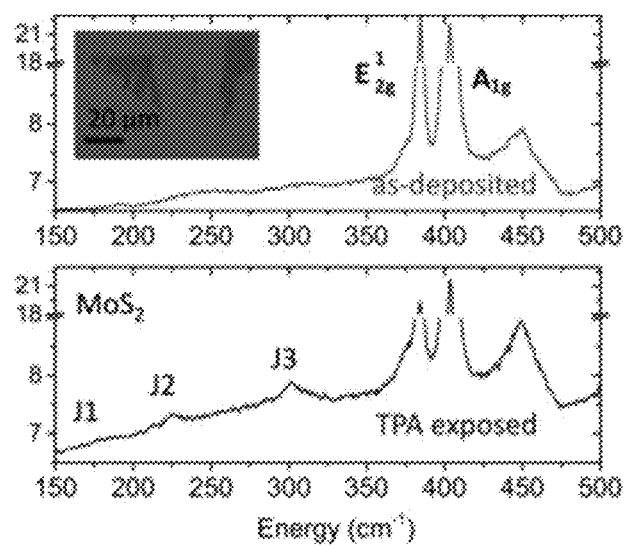

FIGURE 9A FIGURE 9B
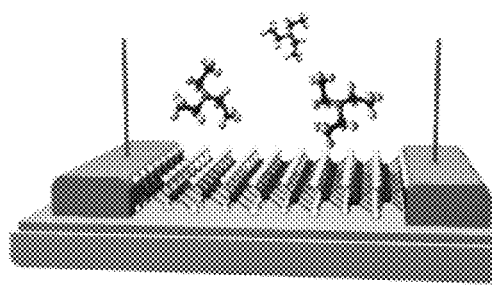
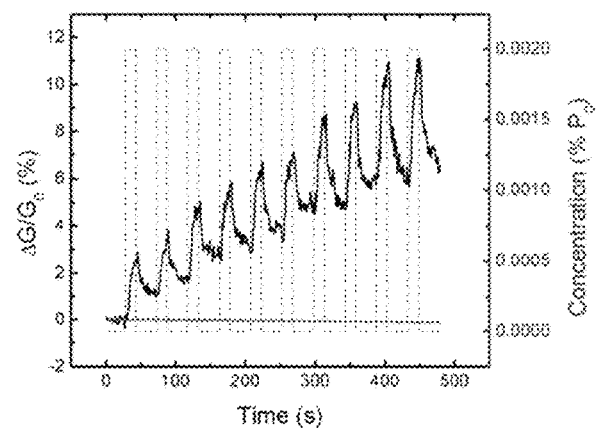
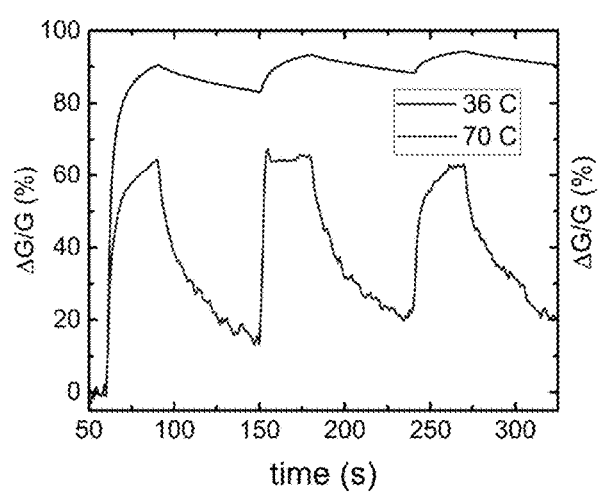
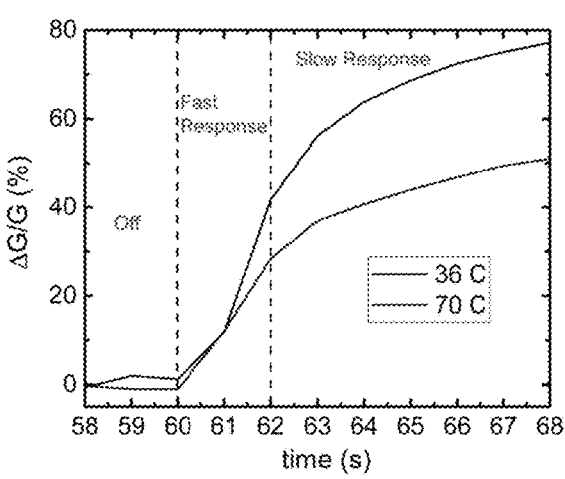
FIGURE 9C FIGURE 9D

FIGURE 10A     FIGURE 10B
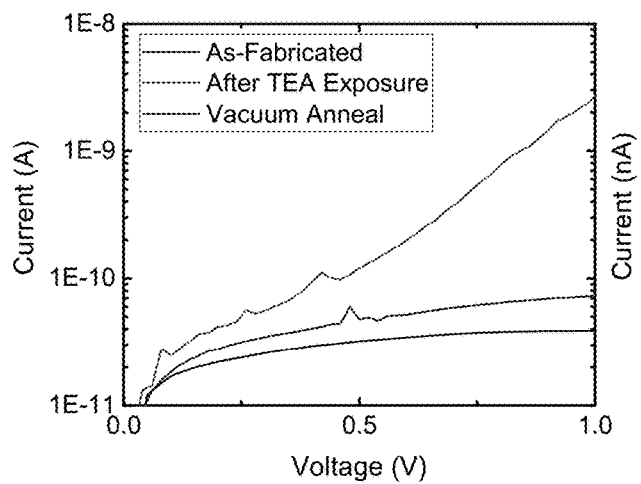
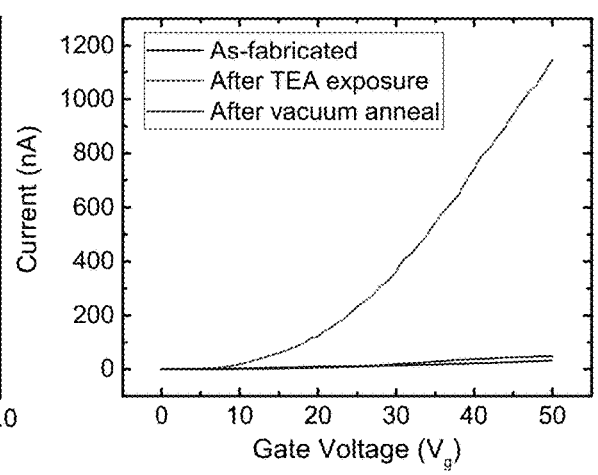

FIGURE 11A      FIGURE 11B
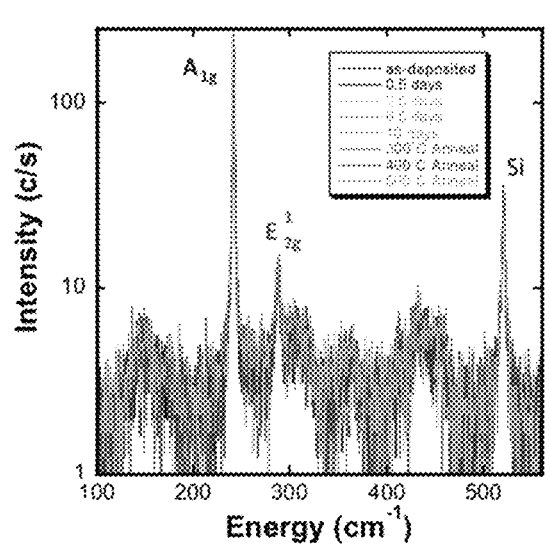
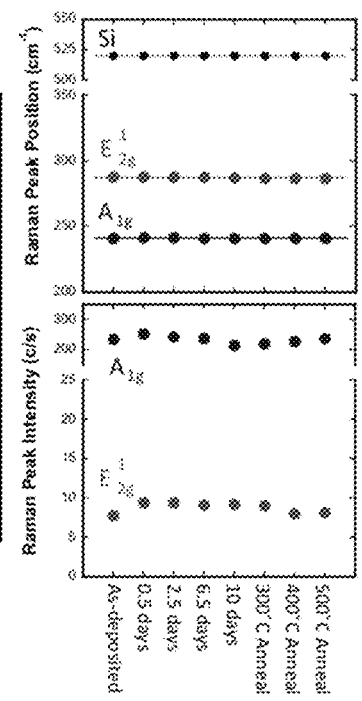
FIGURE 11C

2H TO 1T PHASE BASED TRANSITION METAL DICHALCOGENIDE SENSOR FOR OPTICAL AND ELECTRONIC DETECTION OF STRONG ELECTRON DONOR CHEMICAL VAPORS

CROSS-REFERENCE TO RELATED APPLICATIONS

This application is a divisional application of U.S. application Ser. No. 15/652,491, filed on Jul. 18, 2017, which claimed priority to U.S. Provisional Application No. 62/363,882, filed on Jul. 19, 2016, the contents of each are incorporated herein by reference in their entireties.

TECHNICAL FIELD

This application relates generally to optical and electronic detection of chemicals, and particularly strong electron-donors, by 2H to 1T phase-based mechanisms in transition metal dichalcogenide (TMD) films, detection apparatus incorporating the TMD films, methods for forming the detection apparatus, and detection systems and methods based on the TMD films. The detection apparatus includes a 2H trigonal prismatic phase TMD film that undergoes a transition to the 1T octahedral phase under exposure to strong electron donors. After exposure to an unknown chemical, the TMD film's phase state can be determined to assess whether all or a portion of the TMD has undergone a transition from the 2H phase to the 1T phase. The detection of a change in phase can be used to determine whether the chemical was a strong electron donor.

Following detection, TMD films in the 1T phase can be converted back to the 2H phase, resulting in a reusable chemical sensor that is selective for strong electron donors.

BACKGROUND OF THE INVENTION

Since the discovery that single monolayer films of transition metal dichalcogenides (TMDs) can be isolated from the bulk due to weak interlayer van der Waals bonding, these materials have continued to reveal new and remarkable behaviors and properties.

Devices made from single-layer transition metal dichalcogenides (TMDs) offer the promise of inexpensive, flexible, high-performance electronics that exploit their unique monolayer and surface-dominated geometry. See, e.g., B. Radisavljevic, et al., "Single-layer $MoS_2$ transistors," *Nat. Nanotech.* 6:147-150 (2011); H. Wang, et al., "Integrated circuits based on bilayer $MoS_2$ transistors," *Nano Lett.* 12:4674 (2012); R. Lv, et al., "Transition metal dichalcogenides and beyond: synthesis, properties, and applications of single- and few-layer nanosheets," *Acc. Chem. Res.* 48:56 (2015); and D. Jariwala, et al., "Emerging device applications for semiconducting two-dimensional transition metal dichalcogenides," *ACS Nano* 8:1102 (2014).

TMDs can behave as insulators, semiconductors, metals, magnets, and superconductors, with a variety of properties distinct from bulk. For instance, the semiconductors $MoX_2$ and $WX_2$ transition from indirect gap semiconductors in the bulk to direct gap as monolayers. See G. Kioseoglou, et al., "Valley polarization and intervalley scattering in monolayer $MoS_2$," *Appl. Phys. Lett.* 101:221907 (2012); A. T. Hanbicki, et al., "Measurement of high exciton binding energy in the monolayer transition-metal dichalcogenides $WS_2$ and $WSe_2$," *Sol. State Comm.* 203:16-20 (2015); A. T. Hanbicki, et al., "Anomalous temperature dependent spin-valley polarization in monolayer $WS_2$," *Sci. Rep.* 5:18885 (2016); and K. F. Mak, et al., "Atomically thin $MoS_2$: A new direct-gap semiconductor," *Phys. Rev. Lett.* 105:136805 (2010).

Chemical vapor sensing with monolayers is a particularly promising field, as their inherent few-atom thinness results in extreme sensitivity to surface perturbations. $MoS_2$ is an extraordinarily sensitive chemical vapor sensor, responding selectively to strong electron donors (e.g., amines) through a physisorption process. See F. K. Perkins, et al., "Chemical vapor sensing with monolayer $MoS_2$," *Nano Lett.* 13:668-673 (2013); A. L. Friedman, et al., "Chemical vapor sensing in two-dimensional $MoS_2$ field effect transistor devices," *Sol. St. Elec.* 101:2-7 (2014). A minute quantity of analyte on the surface of the $MoS_2$ acts as an electron donor and local reducing agent, measurably affecting the conductance of the channel.

Differentiation between the 2H and 1T phases using a variety of methods is described in the literature. Conductance measurements provide a means of discriminating between the 2H and 1T phases, with the metallic phase offering a conductance that is significantly higher than the semiconducting phase. Additionally, detailed microscopy measurements such as transmission electron microscopy (TEM) can provide a direct method for visualizing the different phases. However, because these two phases have similar lattice constants and symmetries, and since monolayer samples have small TEM imaging cross sections, such measurements can be extremely challenging. Moreover, due to transferability and optical contrast considerations, the most commonly studied high-quality mechanically exfoliated films are not easily amenable to TEM studies. Optical measurements can be used as differentiation methods because the photoluminescence (PL) readily observed from the semiconducting 2H phase is quenched in the metallic 1T phase. However, because multiple phases can exist in the same TMD film simultaneously, suppression of photoluminescence (PL) is incomplete in a partially transitioned film, resulting in at most a partial reduction in PL. The TMD thin films have also been shown to exhibit additional Raman features (identified as J1, J2, and J3) when it transitions from 2H to 1T.

U.S. Pat. No. 9,063,063 describes a method of making a low-dimensional material chemical vapor sensor comprising exfoliating $MoS_2$, applying the monolayer flakes of $MoS_2$ onto a $SiO_2$/Si wafer, applying a methylmethacrylate (MMA)/polymethylmethacrylate (PMMA) film, defining trenches for the deposition of metal contacts, and depositing one of Ti/Au, Au, and Pt in the trench and resulting in a $MoS_2$ sensor. A low-dimensional material chemical vapor sensor comprises monolayer flakes of $MoS_2$, trenches in the $SiO_2$/Si wafer, metal contacts in the trenches, and thereby results in a $MoS_2$ sensor. A full spectrum sensing suite comprises similarly fabricated parallel sensors made from a variety of low-dimensional materials including graphene, carbon nanotubes, $MoS_2$, BN, and the family of transition metal dichalcogenides. The sensing suites are small, robust, sensitive, low-power, inexpensive, and fast in their response to chemical vapor analytes. The contents of U.S. Pat. No. 9,063,063 are incorporated herein by reference in their entirety.

Co-pending U.S. application Ser. No. 15/479,014, filed on Apr. 14, 2017, describes a method of making a low dimensional material chemical vapor sensor including providing a monolayer of a transition metal dichalcogenide, applying the monolayer to a substrate, applying a PMMA film, defining trenches, and placing the device in an n-butyl lithium (nbl)

bath. A low dimensional material chemical vapor sensor comprises a monolayer of a transition metal dichalcogenide, the monolayer applied to a substrate, and a region or regions comprising the area of electrical contact to the transition metal dichalcogenide that have been treated with n-butyl lithium. The region or regions of the transition metal dichalcogenide treated with n-butyl lithium transition from a semiconducting to metallic phase. Metal contacts on the region or regions of the transition metal dichalcogenide that have been treated with the n-butyl lithium remove the Schottky barrier from the contact area and thereby enhance the selectivity and sensitivity of the sensor device. The contents of U.S. application Ser. No. 15/479,014 are incorporated herein by reference in their entirety.

Chemical vapor sensing devices are currently available, as research tools as well as products available for purchase on the commercial market. Current state-of-the-art conductance sensors (A. W. Snow, et al., "Disordered nanomaterials for chemielectric vapor sensing: A review," IEEE Sens. 15:1301 (2015); surface acoustic wave (SAW) sensors (R. A. McGill, et al., "The 'NRL-SAWRHINO:' A nose for toxic gases," Sens. Actuat. B 65:10 (2000)); and optical chemical vapor sensors (J. W. Grate, "Acoustic wave microsensor arrays for vapor sensing," Chem. Rev. 100:2627 (2000)) achieve high sensitivity, but suffer from drawbacks. Other low-dimensional materials based sensors provide little selectivity, even responding to water vapor, which complicates their utility. Conductance-based sensors can be selective to individual compounds through surface functionalization, but this adds both complexity and expense.

Optical based sensors, like the Drager CMS (Drägerwerk AG & Co. KGaA, Lüeck, Germany), provide portable hand-held chemical vapor sensing. However, they require 1-2 minutes to generate a response, and necessitate a new insertable reading chip every time. Optical-based sensors provide a sensitivity of 5-60 ppm for TEA.

Resistance sensors, such as the Figaro TGS series (Figaro USA Inc., Arlington Heights, IL), are considered state-of-the-art. To sense various gases or mixes of analytes, a new sensor type for each analyte is required. To contain enough surface area for exposure, the sensors are microscale or larger. They require tens of mA for operation. The sensitivity is strongly dependent on temperature and humidity, and they cannot withstand temperatures higher than 200° C., or temperatures down to cryogenic levels. They can detect ammonia-based vapors to a sensitivity of 30-300 ppm.

Surface acoustic wave (SAW) sensors provide chemical class selectivity, being limited by the types of polymers used in the arrayed devices. However, they cannot function well in an environment with large mixtures of chemical vapors and are extremely temperature and humidity dependent.

IMS detectors provide a low-resolution sensing capability with ions separated as ion swarms along a drift tube. Any humidity variance directly affects the swarm size and hence the drift time. As a result, humidity control or correction of IMS detectors is critical. Moreover, with limited resolution the responses of IMS detectors are confounded by mixtures and common household chemicals, food stuffs or military relevant chemicals such as AFFF, a fire fighting foam used ubiquitously by the Department of the Navy and many other Navies. IMS technology is inherently size limited because the drift cell cannot be reduced in size without further compromising selectivity and resulting in increased false alarms. Current state-of-the-art handheld military grade IMS devices (e.g., Lightweight Chemical Detector (LCD) by Smiths Detection, Edgewood, MD, which is used in the Department of Defense's Joint Chemical Agent Detector (JCAD) program), though lightweight and low power when compared to comparable sensors, still weigh 1.5 to 2 lbs, and only last approximately 50 hours on a battery charge.

Mini mass spectrometers are limited by their power consumption to produce vacuum conditions, and as a result hand held or smaller configurations are not practical.

Other low-dimensional material-based sensors provide little selectivity, even responding to water vapor, which complicates their utility. Monolayer graphene sensors have also been proposed. However, graphene does not have a bandgap, which makes it a poor material for FET design, and has low chemical reactivity, making it an unselective as a chemical vapor sensor. Further, the high electron density of graphene means that dipole adsorbates are screened, having no effect on device transport at moderate concentrations.

Unlike TMD sensors, other low-dimensional material-based sensors, such as semiconducting nanowires and nanotubes, show responses that are highly dependent on humidity and temperature, are unselective, or require complicated fabrication techniques. Chemical functionalization of graphene or nanowires can effectively reduce conductivity or create tailored adsorbate binding sites, but adsorbate binding to the additional functional groups, being somewhat displaced from the surface, only weakly affects device conductivity. Moreover, this process adds additional complexity and expense to the resulting devices.

In general, existing sensor technologies lack the combination of high sensitivity and high selectivity required to detect chemical vapors, while providing inherent mechanical flexibility and versatility, and low power consumption.

SUMMARY OF THE INVENTION

The invention described herein, including the various aspects and/or embodiments thereof, meets the unmet needs of the art, as well as others, by providing sensors incorporating TMDs that undergo a phase change from 2H to 1T upon exposure to chemical vapors, particularly vapors from a strong electron donor. Systems incorporating the sensors are also provided. Further, methods for detecting strong electron donors using the sensors are provided, as well as methods for making sensor apparatus and systems incorporating the TMD sensors. The sensors, apparatus, and methods of the invention beneficially permit highly accurate detection of the presence of strong electron donors using a sensor that may beneficially be regenerated and reused multiple times.

In one aspect of the invention, a method for detecting whether an unknown chemical vapor comprises a strong electron donor, includes providing at least one sensor comprising a transition metal chalcogenide thin film comprising at least one region having a 2H phase; exposing the at least one sensor to an unknown chemical vapor; evaluating the transition metal chalcogenide thin film comprising at least one region having a 2H phase to determine whether the phase of the at least one region is 2H or 1T; and detecting that the unknown chemical vapor comprises a strong electron donor if the phase of the at least one region of the transition metal chalcogenide thin film has changed from 2H to 1T.

According to another aspect of the invention, a system for detecting whether a chemical vapor comprises a strong electron donor includes at least one sensor comprising a transition metal chalcogenide thin film comprising at least one region having a 2H phase; an apparatus for evaluating the transition metal chalcogenide thin film comprising at least one region having a 2H phase to assess whether the phase of the at least one region is 2H or 1T; and a transmitter that generates a signal indicating that the chemical vapor comprises a strong electron donor if the phase of the at least one region of the transition metal chalcogenide thin film has changed from 2H to 1T.

According to a further aspect of the invention, a sensor for detecting strong electron donors includes a substrate; a transition metal dichalcogenide thin film comprising at least one first region having a 2H phase; and at least two electrically-conductive leads. At least two second regions of the transition metal dichalcogenide thin film that are directly in contact with the at least two electrically-conductive leads have a 1T phase.

Other features and advantages of the present invention will become apparent to those skilled in the art upon examination of the following or upon learning by practice of the invention.

BRIEF DESCRIPTION OF THE DRAWINGS

FIG. 4A is an optical image of a completed $MoS_2$ FET sensor device, showing electrical evidence of a chemical vapor induced phase change, where the scale bar is 5 m. FIG. 4B is a graph plotting resistance vs. time for the three stages of sensing: (1) The device responds (middle line) to the pulsed strong electron donor triethyl amine (TEA) and is in the 2H semiconducting phase. The peaks are the peaks of the pulses. (2) The devices saturates with analyte and stops responding (upper line). (3) The strong electron donor causes a 2H to 1T phase transition resulting in unresponsiveness to the analyte and a drop in resistance associated with the 1T metallic phase (lower line).

FIG. 5A is an optical image of a monolayer $MoSe_2$ flake (left) and a $MoSe_2$ FET device fabricated from that flake (right). FIG. 5B is a graph showing normalized $MoSe_2$ device conductance as a function of chemical vapor exposure for a typical device. The device stopped responding to analyte vapor at the point where the conductivity is observed to abruptly rise, about $8\times10^8$ Langmuirs. Annealing resulted in the recovery of the original conductance and sensor response. FIG. 5C is a graph showing the response to a pulsed sequence of 0.04% $P_0$ BuAm vapor. The middle line shows the sensor response of the as-fabricated device to a series of pulses (60 s on, 645 s off), and the lower line shows an unresponsive sensor corresponding to $9\times10^8$ Langmuirs in FIG. 5B and with the same series of pulses. Both of these traces go with the bottom x-axis. The upper line (which goes with the top x-axis) shows the recovered response of the device to a series of pulses (30 s on, 160 s off) after annealing at 400° C. in vacuum for 2 hours. FIG. 5D is a graph showing current vs. back gate voltage taken at 1 V for before exposure (middle line), after exposure (upper line), and after annealing the device (lower line).

FIG. 6A is a graph showing a wide-range Raman spectra taken on the monolayer $MoSe_2$ film shown in the inset photographs after a series of exposures to TPA in a bell jar and annealing steps. The black dot on the upper right optical image indicates where the spectra were measured. The middle and lower right images show a superimposition of the integrated intensities of the A1g and E12g and the optical images, attesting to the uniformity of the sample. No significant changes are observed. FIG. 6B is a graph showing Raman spectra taken on the monolayer $MoS_2$ film shown in the optical image in the inset. This shows the spectrum from the as-deposited film. FIG. 6C is a graph showing the spectrum after 7 days exposure to TPA. The relevant peaks are labeled. Each line is an average of 10 points on the film. The appearance of the J1, J2, and J3 peaks in the exposed film is an indicator of the 1T phase.

In FIG. 7F and FIG. 7G, the circles are data for the neutral exciton, the diamonds are for the trion, and error bars are on order of the symbol size.

FIGS. 9A-9D is a depiction of a transmitter sensor device incorporating an $MoS_2$ film, as well as its response to TEA at 100 ppm. FIG. 9A is a schematic of the $MoS_2$ sensor, where the $MoS_2$ layer is set between two Au leads, and a small current is passed while the voltage is monitored. FIG. 9B shows the conductivity response (% change in conductivity as compared to its starting value) as triethylamine (TEA) at 100 ppm, a decomposition by-product of the VX series nerve agents, is pulsed onto the sensor. Peaks in the voltage response correspond to the pulse frequency (dotted upper line, concentration measured as percent of the equilibrium vapor pressure $P_0$). As a baseline test, the lower line shows the response of the device to dry nitrogen only. The slow increase in conductance is attributed to electrostatic charging due to Schottky contacts, and the original conductance is recovered by discharging through a resistor.

Although the conductance of the material changes almost instantly, limitations in the instrumentation speed cause the graphed response to be on the timescale of seconds, obscuring the intrinsic speed of the sensors. FIG. 9C shows the response of a CVD grown $MoS_2$ sensor device to 150 ppm TEA for two temperatures (upper line is 36° C., lower line is 70° C.) and also using 1T phase engineered contacts and 2H phase channel. The electrostatic background is removed by phase engineering (contacts are 1T phase, channel is 2H phase, removing the Schottky barrier). The speed of the response is not affected by temperature, but the sensitivity shows a significant improvement. FIG. 9D shows an enlargement of the response portion of the sensing curve showing a "fast response" time of 2 seconds (upper line is 36° C., lower line is 70° C.). The "slow response" varies and is due to other superfluous chemical effects.

FIG. 10A is a semi-log plot of current vs. voltage for an as-fabricated, saturation-dosed, and vacuum annealed $MoSe_2$ device. FIG. 10B shows current vs. gate voltage for the device presented in FIG. 5D with a wider range than was presented there.

FIG. 11A is an image of the same Raman data as plotted in FIG. 6A on a log-plot showing that there are no additional peaks in the spectra arising out of the noise. FIG. 11B depicts the peak positions as a function of exposure or annealing event for both the $A_{1g}$ and $E_{12g}$ peaks. FIG. 11C depicts the peak power as a function of exposure or annealing event for both the $A_{1g}$ and $E_{12g}$ peaks.

DETAILED DESCRIPTION OF EMBODIMENTS OF THE INVENTION

The invention described herein, including the various aspects and/or embodiments thereof, meets the unmet needs of the art, as well as others, by providing apparatus, systems, and methods for the optical and/or electronic detection of chemicals, and particularly strong electron-donors. The detection is based on the 2H to 1T phase change of transition metal dichalcogenide (TMD) films upon exposure to chemical vapor. The invention includes detection apparatus incorporating the TMD films, methods for forming the detection apparatus, and detection systems and methods based on the TMD films.

The invention utilizes the 2H semiconductor to 1T metallic phase transition in TMD films to create a chemical sensors, sensor arrays, systems, and methods which can detect a wide range of chemical types, from permanent gases to nerve agents. Chemicals that may be detected using the sensors, systems, and methods of the invention include toxic industrial chemicals (TICs) and chemical warfare agents (CWAs) that are strong electron donors, as may be determined by those skilled in the art. These chemicals include, but are not limited to, amines (i.e., TEA (triethylamine), TPA (tripropylamine), BuAm (butylamine), ammonia), arsines, acetone, acetonitrile, pyridine, DMSO (dimethylsulfoxide), DMMP (dimethyl methylphosphonate), TATP (triacetone triperoxide), and derivatives of phosphonic acid (i.e., the V-series nerve agents, VE (O-ethyl-S-[2-(diethylamino) ethyl] ethylphosphonothioate), VG (O,O-diethyl-S-[2-(diethylamino)ethyl] phosphorothioate), VM (O-ethyl-S-[2-(diethylamino)ethyl]methylphosphonothioate), VX (O-ethyl S-(2-diisopropylaminoethyl) methylphosphonothioate)). Explosive chemicals that are strong electron donors may also be detected using the sensors, systems, and methods of the invention, including, but not limited to, TNT (2-methyl-1,3,5-trinitrobenzene), TEX (4,10-dinitro-2,6,8,12-tetraoxa-4,10-diazatetracyclo[5.5.0.0$^{5,9}$.0$^{3,11}$]-dodecane), HMX (octahydro-1,3,5,7-tetranitro-1,3,5,7-tetrazocine), CL-20 (2,4,6,8,10,12-Hexanitro-2,4,6,8,10,12-hexaazatetracyclo [5.5.0.0$^{3,11}$.0$^{5,9}$]dodecane), and RDX (1,3,5-trinitro-1,3,5-triazinane), as well as additional explosives as may be determined by those skilled in the art.

The chemicals may be detected by contacting the sensors of the invention with an unknown chemical provided in solid, liquid, or gas form so long as the molecules of the unknown chemical are able to react with the TMD film. When the chemical is provided as a solid or liquid, it is preferably diffused or suspended in a gaseous medium (i.e., air, or an inert gas such as argon or other noble gases, and nitrogen ($N_2$)) to form a vapor comprising the solid or liquid as fine particulates/droplets.

Figure 1:
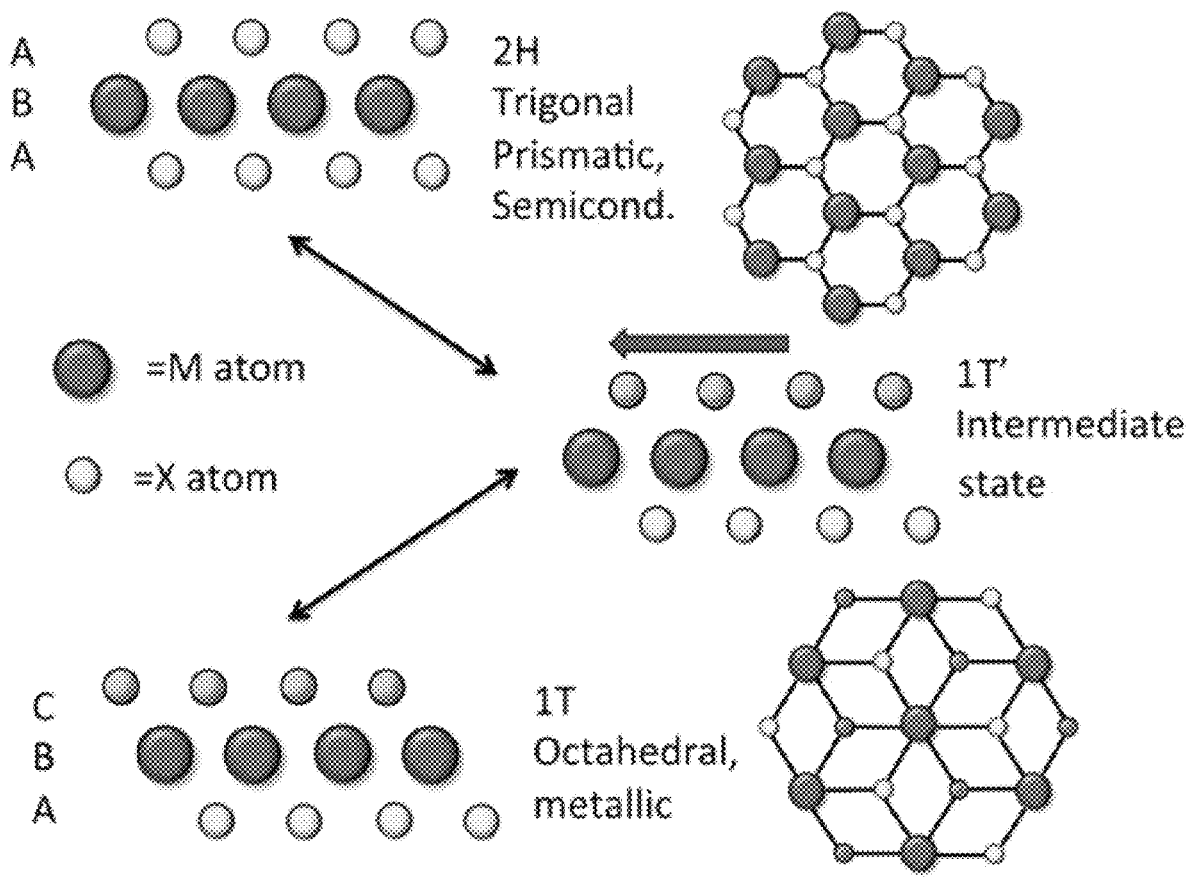
FIG. 1 is a diagram of the 2H to 1T phase transition in a transition metal dichalcogenide (TMD).

The 2H-1T transition is driven by excess strain or charge in the TMD lattice. For most of the TMDs, the lowest energy, stable configuration is the semiconducting, tetrahedral 2H formation, where the three chemical planes in a single monolayer are stacked in an A-B-A sequence. Lattice strain in the TMD, which can be caused by excess charge delivered by surface dopants, can force the material first into an intermediate, unstable 1T' state and then into the metastable metallic, octahedral 1T state. Here, the atomic planes are stacked as C-B-A in a local energy minimum. Schematic depictions of these various phases are presented in FIG. 1. The 2H and 1T phases are differentiated both by conductance measurements, with the metallic phase offering lower resistance (at least an order of magnitude lower), and optical characterization.

After exposure to an unknown chemical, which may be provided in vapor form, the TMD film's phase state is determined to assess whether all or a portion of the TMD has undergone a transition from the 2H phase to the 1T phase. The detection of a change in phase can be used to determine whether the detected chemical was a strong electron donor. Following detection, TMD films in the 1T phase can be converted back to the 2H phase, resulting in a reusable chemical sensor that is selective for strong electron donors. The TMD film's phase state can be determined by techniques including Raman spectroscopy, photoluminescence spectroscopy, and electronic resistance measurements to determine if the vapor was a strong electron donor.

The sensors, systems, and methods of the invention encompass: (1) isolating TMD materials from the bulk either by mechanical exfoliation or direct growth with chemical vapor deposition, (2) fabricating devices and exposing them to various analytes of interest, and (3) performing analysis of the phase state and chemiresistive response following exposure in order to determine whether the analyte is a strong electron donor.

The sensors, systems, and methods of the invention are capable of rapid, sensitive, and selective detection of a wide range of hazardous gases and vapors in an ultra-low power, small footprint system, together with a path for low-cost production. The sensors of the invention exceed the state-of-the art in performance metrics selected from the group consisting of: sensitivity, selectivity, speed, refresh rate, and the SWaPC criteria (size, weight, power, cost).

These and other aspects of the invention are discussed in further detail below.

TMD Compositions

Transition metal dichalcogenide (TMD) materials for use in the apparatus and methods of the invention have the chemical formula $MX_2$, where M is a transition metal, and X is a chalcogen.

Transition metals include elements from Groups 3-12 of the periodic table. The transition metals include Sc, Ti, V, Cr, Mn, Fe, Co, Ni, Cu, Zn, Y, Zr, Nb, Mo, Tc, Ru, Rh, Pd, Ag, Cd, La, Hf, Ta, W, Re, Os, Ir, Pt, Au, Hg, Ac, Rf, Db, Sg, Bh, Hs, Mt, Ds, Rg, and Cn, as well as the lanthanide series elements (La, Ce, Pr, Nd, Pm, Sm, Eu, Gd, Tb, Dy, Ho, Er, Tm, Yb, and Lu), and actinide series elements (Ac, Th, Pa, U, Np, Pu, Am, Cm, Bk, Cf, Es, Fm, Md, No, Lr). Preferred transition metals for use in the apparatus and methods of the invention include Mo, W, Nb, Hf, Ta, and V, with Mo, W, Nb, and Ta being particularly preferred.

Chalcogens include the elements found in Group 16 of the periodic table. The chalcogens include O, S, Se, Te, and Po. Preferred chalcogens for use in the apparatus and methods of the invention include S, Se, and Te, with S and Se being particularly preferred.

Preferred TMD materials have a 2H crystal structure that is semiconducting in nature, and are capable of undergoing a transition to a 1T crystal structure that is metallic in nature. In some aspects of the invention, preferred 2D TMD materials for use in the sensors, systems, and methods may be selected from the group consisting of $MoS_2$, $MoSe_2$, $WS_2$, $WSe_2$, $NbS_2$, $NbSe_2$, $TaS_2$, $TaSe_2$, and combinations thereof. Additional TMD materials formed from the transition metals and chalcogens set forth above are also within the scope of the invention.

Each TMD composition requires a different amount of energy to transition between phases. For the $MoX_2$ films, the energies required for a 2H to 1T transition $\Delta E(2H \rightarrow 1T)$ are such that $\Delta E[MoS2] > \Delta E[MoSe2] > \Delta E[MoTe2]$. Excess charge from adsorbates either on or otherwise incorporated in the TMD can also stabilize the 1T state, which can be relaxed back into the 2H state by thermal annealing. This has been demonstrated by treating a $MoS_2$ monolayer with n-butyl lithium, a strong electron donor. Even after the n-butyl lithium is completely removed from the surface and no longer actively donates charge to the film, the film remains in the 1T phase. In view of the different transition energies for different TMD compositions, according to one aspect of the invention, two or more TMD compositions may be used simultaneously, either within one sensor, or in multiple sensors used within a system, in order to provide additional detection capabilities.

The TMD materials of the invention may be provided as thin films, where the term "thin film" encompasses films having fewer than ten crystalline layers of the TMD material, preferably fewer than five crystalline layers of the TMD material, and more preferably the TMD thin film has one or two crystal layers (i.e., the TMD thin film is provided as a monolayer or bilayer film). Each crystal layer $(MX_2)$ is one molecule, or three atoms, thick. Such materials may also be referred to as two-dimensional (2D) due to their very thin nature. Thin films are preferred in accordance with the invention in order to facilitate detection of the crystal structure of the material, and detection of changes to the crystal structure.

The use of 2D or thin TMD films that are atomically/ molecularly thin offers advantages when used in the sensors, systems, and methods of the invention. The 2D TMD films are at the extreme limit of surface to volume ratio and have the potential to provide an instantaneous response to an analyte exposure. In addition, sensitivity to single atom perturbations from analyte binding can be achieved. The TMD phase transition can contribute an additional sensing paradigm, delivering a truly multimodal (phase and chemiresistive response) chemical vapor sensor.

Monolayer TMDs provide the basis for inexpensive, flexible, high-performance sensors of the invention that exploit their unique surface-dominated functionality. Monolayer TMDs include insulators, semiconductors, metals, and other types of materials with a variety of properties not observed in the bulk. For example, the materials $MoX_2$ and $WX_2$ are semiconductors that transition from indirect gap in the bulk to direct gap as monolayers, and have shown field effect transistor (FET) on/off ratios and room temperature mobilities that are competitive with existing sensing devices. Additionally, these materials are useful in chemical vapor sensing applications because the inherent few-atom-thickness of the material greatly enhances their sensitivity to even the smallest surface perturbations. Certain films respond selectively to strong electron donors through a physisorption process. A minute quantity of analyte lying on the surface of the TMD acts as an electron donor and local reducing agent, which measurably affects the conductance of the film.

A conducting sheet of $MoS_2$, for example, is an extraordinarily sensitive gas sensor, responding selectively to strong electron donors through a physisorption process. A nanoscopically small quantity of analyte on the surface of the $MoS_2$ acts as an electron donor and local reducing agent, measurably affecting the conductance of the channel. Indeed, the theoretical limit of detection for the 2D TMD materials of the invention is a single molecule, potentially making the sensors incorporating these materials the most sensitive field portable devices ever created.

TMD Sensors

The sensors of the invention encompass any sensor structure that incorporates a layer of one or more transition metal dichalcogenides (TMDs) that are capable of undergoing a transition from a 2H semiconducting phase to a 1T metallic phase. The semiconductor-metal 2H-1T phase transition in TMDs creates a route towards electronic device engineering of either the channel or the contacts in a reversible, repeatable, non-damaging, and robust manner. The determination of whether or not the TMD films are in the 1T or 2H phase after exposure to an unknown chemical vapor constitutes a new class of chemical vapor sensor.

A sensor for detecting strong electron donors in accordance with the invention includes a substrate and a transition metal dichalcogenide thin film comprising at least one first region having a 2H phase that is provided on the substrate. The sensor may optionally also include at least two electrically-conductive leads, for example, in order to form a field effect transistor (FET). Where electrically-conductive leads are provided, they are preferably placed on directly in contact with regions of the TMD thin film that have been engineered to have a 1T phase in order to avoid Shottky barriers.

Sensors of the invention may be formed by providing a 2D TMD film between two leads, which may be formed of conductive materials including, but not limited to, gold, titanium, chromium, platinum, palladium, copper, silver, aluminum, and alloys and combinations thereof. The invention is not to be considered limited by the composition of the leads. The specificity of the sensors also depends on the phase of the contacts. A 2H/2H phase contact/channel n-type device will respond to both electron donors and polar molecules, while a 1T/2H phase contact/channel n-type device will only respond to electron donors. As most nerve agents and explosives of interest (e.g., VX, TATP/acetone based explosives, amine-based explosives) are either polar molecules or strong electron donors, the sensors of the invention are beneficially selective to the types of analytes that are most relevant to industrial, security, and military applications. Furthermore, by using the multimodal response that combines the phase state and chemiresistive nature of TMD sensors, a clear path exists toward analyte identification based on distinct optoelectronic fingerprints of individual analytes. For example, stronger electron donors will result in a greater magnitude chemiresistive response, as more charge will be transferred to the TMD lattice, and the corresponding reduction in photoluminescence will also be greater as compared to weaker electron donors. As an additional advantage, the TMD-based sensors of the invention do not respond to water vapor, allowing their use without correction or remediation for humid air.

By engineering the phases of the contacts applied to the sensor devices, their selectivity and signal-to-noise ratio can be increased. The Schottky barrier present in a device where both the contacts and the channel are composed of 2H phase material results in a sensor that responds to polar molecules (such as ketones or alcohols) as well as electron donors, and exhibits an ever-increasing base conductance due to electrostatic charging (shown in FIG. 9B). However, by selectively treating the contacts areas with n-butyl lithium prior to metallization, converting the treated area from 2H phase to 1T phase, the Schottky barrier is eliminated. This results in no adverse response to polar molecules and removes the background from the device response. Large-area films grown by CVD, such as the devices that produced the data in FIGS. 9C and 9D, yield the same results as exfoliated films, thus paving the way towards the inexpensive manufacture of devices.

TMDs are inherently ambipolar semiconductors, with their Fermi energy strongly dependent on interactions with a particular support substrate. Exemplary support substrates include, but are not limited to, silicon, silicon dioxide, aluminum oxide, sapphire, germanium, gallium arsenide, alloys of silicon and germanium, indium phosphide, polypropylene, polyethylene, polyethylene naphthalate, polyether ether ketone, polycarbonate, polyethersulfone, polyimide, and combinations thereof. In some aspects, the sensors have been fabricated on $SiO_2$, which gives an n-type behavior. Therefore, these sensors are selective to strong electron donor analytes (e.g., the phosphonate nerve agents and ammonia). For p-type materials, TMD sensors have shown selectivity to electron acceptor analytes.

The sensors of the invention may also include a means for communicating with other elements of the systems described herein, or directly with the wearer of the sensor. The communications may be direct visual assessment (as in the case of reduced photoluminescence), or by transmitting a signal based on the conductivity of the TMD film. In some aspects of the invention, the sensors include an electromagnetic signal transmitter, such as a radio transmitter.

The sensors of the invention preferably comprise a single molecular layer of TMD, and are therefore beneficially small and lightweight as compared to other sensors. For example, the weight of a TMD sensor in the field would be entirely determined by the power source or other packaging used to support the TMD layer. The sensors of the invention can be provided in the amount of space available on a button for clothing, or even smaller. Additionally, because the TMD films of the invention are inherently flexible and can be put on a variety of flexible substrates (such as flexible polymers), they can be deployed as sensors in a variety of ways not easily amenable to other sensors. For example, they can be integrated into clothing (e.g., worn as patches or even coated directly onto fabric), gas masks, ColPro systems, or they can be pasted like decals onto ships, planes, and other vehicles, while adding practically no additional weight. The benefits of these devices are promising in households, and for automotive/aerospace use, in addition to industrial, security, and military applications.

TMD-based sensors have very low power requirements, operating with 1 microampere or less of current, thus reducing the power supply footprint. Power sources that may be used in the sensors of the invention include electrochemical cells, solar cells, fuel cells, and capacitors, though additional types of power sources are envisioned for use in accordance with the sensors of the invention.

TMD films can be readily grown on large area wafers using inexpensive CVD methods and require no complex components for operation. Therefore, they provide a highly cost-effective sensor technology.

The TMD sensors of the invention offer the low power, high selectivity, high sensitivity, ease of use, robustness, versatility, mechanical flexibility, and low fabrication expense. By incorporating phase engineering of the contacts, the TMD sensors described herein are even more low-power and selective. The sensing behavior is therefore not overwhelmed by Schottky barriers or the behavior of the contacts, which allows the intrinsic chemical vapor sensing properties of the film to dominate.

The TMD sensors of the invention have the potential to detect many different analytes with a single sensing apparatus. They are inherently nanoscale, necessitating minimal space for a sensor. For example, the sensors of the invention may have an area of less than 1 $cm^2$, permitting them to be applied to a variety of materials, personnel, and equipment, although larger sensor areas are also envisioned within the scope of the invention. As the sensors themselves are only atoms thick and microns in area, the size is entirely limited by the power source. Standard, currently available watch batteries (e.g., button-type batteries), which are approximately 1 $cm^2$ in are would provide 2500-25,000 hours of continuous operation, depending on whether an embedded heater is used to clean the device periodically between exposures. They require less than 1 µA of current for operation. They can operate over a wide range of environmental conditions, from cryogenic temperatures (i.e., from 0 K to 123 K) to over 600° C., and have no dependence on humidity. These benefits are provided while achieving detection sensitivity that is similar (e.g., approximately equal) to the sensitivity of currently-available sensors, and is on the order of tens of parts per billion. For example, analytes relevant to identifying explosives and nerve agents have been detected to concentrations as low as 10-50 parts per billion (ppb) by monitoring the conductance of a simple $MoS_2$ field effect transistor (FET). The TMD sensors of the present invention are also multiuse, and respond quickly after exposure to an analyte.

The TMD sensors of the invention can be used repeatedly, with a refresh rate on the order of seconds. However, eventually, given enough exposure, the entire film will transition to the 1T phase. The sensors described herein incorporate TMD films that can beneficially be converted from the 1T phase back to the 2H phase, for example, by annealing. The invention is therefore able to provide a reusable chemical vapor sensor that is selective for strong electron donors. This can be accomplished by incorporating an in-situ heating element into the sensor apparatus, although separate means for application of heat are also within the scope of the invention, for example, by using a hand-held heat gun, or depositing the sensors in an oven after the phase change has occurred. Other techniques may be used for converting the 1T phase TMD back to the 2H phase are also within the scope of the present invention. The ability to convert the 1T phase TMD film back to the 2H phase permits the sensors of the invention to be reused multiple times, and preferably the sensors can be reused infinitely. However, if the integrated exposure-based transition is not being used as a concurrent sensing method (like a dosimeter), given the size and expense of the hypothetical device, it could simply be discarded and replaced with a fresh film rather than annealing it.

The sensors described herein provide a combination of high sensitivity and high selectivity, while providing inherent mechanical flexibility (and thus, versatility), environmental robustness, low-power requirements (only nanoWatts of power are dissipated in operation), low-dimensionality, speed and ease of use, portability, and inexpensiveness. Moreover, the sensors of the invention are the first to use the detection of a crystal phase change to identify the presence of strong electron donor chemicals in vapor form. These are all distinct advantages over conductance-based or optical-based chemical vapor sensors. Thermal annealing can be used to clean the sample of physisorbed analyte, rendering the sensors reusable almost indefinitely.

The estimated response time for the sensors of the invention is less than 10 seconds, preferably from 1-5 seconds. However, this is likely due to equipment limitations and not a reflection of the absolute detection speed of the material. The "fast response" time of the devices of the invention is approximately 2 seconds, as shown in FIG. 9D, which is an enlargement of FIG. 9C. However, in some devices, speeds of 200 ms have been achieved. The relative strength of the electron donating analyte can contribute to the response time. Faster charge transfer will result in faster response from the sensor. The "slow response" time is likely not due to physisorption, which is the primary mode of sensor response of these devices, but to other mostly superfluous chemical processes. The "slow response" varies for each pulse and, for the most part, can be ignored, as it does not affect or limit the fast response time. However, slow responses as quick as 500 ms have been achieved. Therefore, while the "fast" response time is an intrinsic property of the device, the "slow" response time is an extrinsic property and can be tuned and mitigated as more pristine material is fabricated. Heating the devices increases their signal-to-noise-ratio and sensitivity. DFT calculations have shown that the binding energies for physisorption of relevant molecules are 10-200 meV, depending on the site chemistry and the model used. This is on the order of room temperature (~25 meV). Thus, although spontaneous desorption is expected, elevated temperatures can exponentially accelerate the process and thus greatly lower the response time. The limit of detection speed is likely related to the speed of physisorption and charge transfer from the analyte to the film, and could theoretically be practically instantaneous. The full realization of the kinetic potential of the TMD sensor of the invention would permit them to be used for micro gas analyzers, where a micro gas chromatograph needs a miniature fast responding sensor capable of detecting a wide range of chemicals.

Overall, the 2D TMD-based sensors of the invention are particularly selective for TICs, CWAs, and explosives, and their multimodal response also gives them an advantage in selectivity over other sensor technologies. Although their refresh rate is on order of seconds (chemiresistive response) or longer (phase-based response) as compared to other technologies, their low expense and small footprint enables them to be easily exchanged or for multiple sensors to be used simultaneously. The TMD sensors of the invention are extraordinarily sensitive, fast transducers that can be used for multiple targets in any given battlefield environment at lower size, weight, power and cost, distinct advantages over other chemical sensing technologies.

Systems

The systems of the invention for detection of chemicals include exposing the TMD film or sensor device to an unknown chemical that may contain one or more strong electron donors.

Analytes relevant to TICs, CWAs, and explosives may beneficially be detected in the low parts per billion (ppb) using these systems. Such sensitivity is at relevant threat level for CWAs and comparable to the current state-of-the-art for ion mobility spectrometers (IMS), mini mass spectrometers, resonators, conductance-based sensors, and optical chemical vapor sensors. For example, the presence of these analytes may be monitored by tracking the conductance of a simple $MoS_2$ back-gated FET (see FIGS. 9A-9D).

The systems of the invention for detecting whether a chemical vapor comprises a strong electron donor include at least one sensor comprising a transition metal chalcogenide thin film comprising at least one region having a 2H phase. Preferably, multiple sensors are provided that are capable of gathering information from a variety of sources, and locations. In some aspects of the invention multiple different TMD film compositions may be used in the sensors included within the system, either by including more than one TMD film composition in a single sensor, or by including multiple sensors each including a single TMD film where not all sensors have the same TMD film composition, or a combination of both types of sensors.

The systems of the invention include apparatus for evaluating the transition metal chalcogenide thin film comprising at least one region having a 2H phase to assess whether the phase of the at least one region is 2H or 1T. The apparatus for evaluating the transition metal chalcogenide thin film may be a Raman spectrometer, a photoluminescence spectrometer, or an electronic resistance sensor, although the invention is not limited to these detection means. Any device capable of determining the phase of a region of interest of the TMD film may be used in the systems of the invention. In some aspects of the invention, the apparatus for evaluating the TMD thin film may also be included as a component of the sensor. In additional aspects of the invention, more than one technique or apparatus for determining the phase of the TMD film may be used concurrently for more accurate phase identification.

The systems of the invention may also optionally include at least one transmitter that generates a signal indicating that the chemical vapor comprises a strong electron donor if the phase of the at least one region of the transition metal chalcogenide thin film has changed from 2H to 1T. Incorporation of the transmitter is beneficial in order to allow information regarding the detection (or non-detection) of a strong electron donor to be relayed to remote locations and users. When provided, the transmitter may be included as a component of the sensor, or as part of the apparatus used to evaluate the TMD thin film of the sensor.

The detection systems of the invention may also include means for annealing the TMD thin film to return the film to the 2H phase. The systems of the invention are therefore able to reuse the chemical vapor sensors. This can be accomplished by incorporating an in-situ heating element into the sensor apparatus, although separate means for application of heat are also within the scope of the invention, for example, by using a hand-held heat gun, or an oven for depositing the sensors after the 1T phase change has occurred. Other apparatus that may be used for converting the 1T phase TMD back to the 2H phase are also within the scope of the present invention.

The detection systems described herein may be used, for example, in active electronic sensing systems, and passive optical sensing systems. For active electronic sensing, the conductance of a TMD field effect transistor (FET) device is monitored as it is exposed to chemical vapors. If the resistance drops and the device ceases to respond, then it has tested positive for a strong electron donor. For passive optical sensing, the TMD films can be conformally pasted on vehicles or incorporated into clothing. A commercially available, hand-held Raman or photoluminescence (PL) spectroscopy device can be used to periodically read the film properties. If the film shows a decrease in PL, or exhibits the J1, J2, and J3 peaks, then the sensor has tested positive for a strong electron donor.

The detection systems incorporating the 2D TMD films and sensors of the invention may be beneficially incorporated into security and defense applications, although they are not to be considered limited to these applications. Development of new technologies to detect for a wide range of toxic industrial chemicals (TICs) and chemical warfare agents (CWAs) is a critical challenge for security and defense. The vast majority of TICs, CWAs, and explosives or related chemicals are strong electron donors or acceptors. Charge transfer from adsorbed molecules of any of these agents enables sensitive electronic detection. By utilizing single molecular layers of two-dimensional 2D TMD films, which are electronically sensitive to CWA simulants, it is possible to establish a multimodal sensing platform that will combine optical (photoluminescence and Raman) responses to identify and screen target analytes in real time with high fidelity. The 2H and 1T phases are differentiated both by conductance measurements, with the metallic phase offering a resistance that is at least an order of magnitude lower, and optical measurements. This type of diffusionless phase change can occur locally and proceed across the surface rapidly. Although the exact speed of the phase change is unknown, theoretical estimates predict a nanosecond or less for typical sample geometries.

The sensors and systems of the invention use the 2H to 1T phase transition as either a concurrent or a stand-alone method for detecting and identifying chemical compounds of critical interest to the user, who in some aspects of the invention may be a security professional, an industrial safety professional, a member of law enforcement, or a warfighter. The presence of a strong electron donor on an n-type TMD film induces a phase change from the 2H state, while the presence of a strong electron acceptor will cause a phase change from the 1T state. Likewise, for a p-type TMD film, modulation will occur in the 2H state for acceptor analytes and in the 1T state for donor analytes. As the amount of charge required to create a phase change in each TMD material is different (bandgaps for several TMDs, which are proportional to the energy required for a phase change: $MoS_2$=1.89 eV, $MoSe_2$=1.58 eV, $WS_2$=2.05 eV, $WSe_2$=1.61 eV), a suite of concurrently sensing TMD materials can allow electron donors/acceptors of varying strengths to be sensed and even identified with the necessary redundancy to minimize false alarms. Furthermore, the phase transition is reversible an unlimited number of times with spot annealing, the TMDs are inherently flexible, and they are inexpensive to produce. Therefore, sensors and systems of the invention provide a chemical vapor sensing ability that is ultra-low power, mechanically flexible yet robust, highly sensitive, highly selective, versatile, and inexpensive. The sensors include a 2H trigonal prismatic phase TMD that undergoes a transition to the 1T octahedral phase under exposure to strong electron-donor chemical vapors.

In addition to providing multiple sensors using different TMD materials, the systems of the invention envision combining 2D TMD sensors with other currently-available sensors, including, but not limited to, conductance-based sensors, optical-based sensors, surface acoustic wave (SAW) sensors, IMS detectors, and mini mass spectrometers.

The phase state of the TMD film (i.e., the non-photoluminescent and conductive metallic 1T phase in which the $E_{2g}$ line is not observed by Raman spectroscopy, but J1, J2, and J3 signals are observed; or the photoluminescent semiconducting 2H phase) can be read by techniques including Raman spectroscopy, photoluminescence spectroscopy, and electronic resistance measurements to determine if the vapor is a strong electron donor. After exposure to a strong electron donor, the TMD film exhibits decreased photoluminescence, and increased conductivity. Either or both of these properties may be measured in order to assess the TMD film or sensor device following exposure to a chemical. Although a highly-surface-doped 2H phase film can be very conductive, only a 1T-phase film will show an abrupt change in conductance at the transition point and remain relatively stable in a variety of conditions (vacuum, annealing below the transition temperature, etc.) that would otherwise remove surface dopants and cause a loss of conductance for the surface doped 2H-phase film.

After the TMD film or sensor has been exposed to a chemical vapor in order to determine whether a strong electron donor is present in the vapor, the TMD of the sensor may remain in its 2H phase if no strong electron donor was detected, or the TMD may be in its 1T phase if a strong electron donor was detected. If no detection has occurred, then the sensor may be used again without further intervention. However, if detection of a strong electron donor has occurred, the TMD film will be in its 1T crystal phase, and further processing may be required before the sensor can be used again to detect a strong electron donor. The TMD film of the sensor may be converted back to its original 2H phase by techniques including, but not limited to, annealing.

Security and military personnel in particular require ever more compact, lightweight sensor equipment for detecting hidden explosives, drugs, nerve gases, and other harmful, possibly weaponized, chemicals. The sensors of the invention based on monolayer TMDs are 2D materials dominated by surface effects, making them sensitive to single atomic perturbations by airborne molecules and allowing the sensors to obtain single atom sensitivity and nearly instantaneous response times. The sensors require very little power for conductance-based sensing, using only small, off-the-shelf, commercial batteries. The sensors are inherently flexible and can be attached to the hulls of ships, to the fuselages of drones and planes, or even incorporated directly onto uniforms of soldiers in the field. The sensors can be operated in real-time through conductance measurements or incorporated with now-available pocket size lasers for optical interrogation in the field, giving a truly multimodal response capability. They can even be used solely for passive measurements. For example, a sheet of TMD could be attached to a drone and flown into an area of interest. When the drone returns, a quick scan from a hand-held Raman device or using a small hand-held Ohmmeter will determine if explosives, nerve gas, or other chemical compounds of interest are in the area. Overall, the systems of the invention address the need for high-speed, low-power electronics and information processing, reducing power and battery requirements for personnel equipment and various platforms including unmanned aerial vehicles, sea platforms, and sensors.

The systems of the invention incorporate the sensors into a device that may be carried or worn by one or more personnel at risk of exposure to strong electron donors. Preferably, multiple personnel dispersed across an area are outfitted with the sensors in order to provide information regarding where strong electron donors are detected within the area.

The device may beneficially be connected to a controller programmed to monitor signals from multiple sensor devices and determining where strong electron donors are present. The controller may also be programmed to send a responsive signal to users wearing the devices to indicate that a strong electron donor has been detected in the area, and optionally an indication of the portion of the area where the strong electron donor was detected. The responsive signal may be received by the sensor device itself. The responsive signal may also be received by a different communication-enabled apparatus, which may be co-located with the sensor, or located remotely from the sensor. The sensor may be configured with any necessary components required to form a transmitter, transmitter-receiver, or transceiver, as would be understood by those skilled in the art of fabricating such devices.

The signals transmitted from the sensor device to the controller may be any form of signal capable of being generated and detected, preferably radio waves (i.e., electromagnetic waves of frequencies from 3 Hz to 3,000 GHz, propagated in space without artificial guide). Radio waves may be transmitted using technologies such as cellular (such as 1G, 2G, 3G, 4G, 5G, LTE, LTE-Advanced), infrared, Wi-Fi, Wireless USB, and Bluetooth. The systems of the invention are not limited by the particular communication method selected. The signal may also be light-based (visible, infrared, ultraviolet). Where electromagnetic waves are used to transmit light-based signals, optical detection equipment may be utilized to identify the signals.

Methods

The methods of the invention encompass methods for forming the sensors of the invention, as well as methods for detecting exposure to strong electron donors by monitoring transitions that occur within the sensor.

TMD films for use in the apparatus and methods of the invention may be formed, for example, by exfoliating layers from the bulk TMD and placing them on a substrate, or depositing layers directly on a substrate in liquid or vapor form. Where the film is formed by exfoliation, mechanical exfoliation may be performed using an adhesive (i.e., tape), liquid exfoliation (i.e., lithium intercalation), sonication, microwaves, and shear forces generated using surfactants or organic solvents. Deposition may be performed by depositing a thin layer of a precursor to the TMD, followed by annealing and sulfurization. The invention is not to be construed as limited to any particular film deposition technique, so long as the TMD film is capable of undergoing a detectable transition from the 2H crystal structure to the 1T crystal structure.

The methods of the invention may also include the use of chemical vapor deposition (CVD) growth methods to produce large areas of TMD films, which may then be used to fabricate devices from the films using techniques that include, but are not limited to, a combination of Deep-UV and electron beam lithography.

The device size, shape, and dimensions may be varied in order to achieve maximum sensitivity and response. In addition to the TMD film, the sensors of the invention include a substrate supporting the film. Substrates for use in the sensing apparatus of the invention include, but are not limited to, silicon, silicon dioxide, aluminum oxide, sapphire, germanium, and gallium arsenide. For field applications, the sensor TMD film may be applied to a flexible substrate that is then applied to plastics, fabrics, and structural panels of buildings and vehicles, without limitation.

The sensors of the invention may be formed by incorporating one or more contacts provided on the TMD film. In some aspects of the invention, the sensor is provided as a field effect transistor (FET), but other device structures are envisioned for use as sensors in accordance with the invention. The contacts for the FET sensor device (i.e., source, drain, and gate terminals) may be selectively engineered Ohmic contacts, which exhibit a linear current-voltage (I-V) curve.

The electrical contacts may be applied to the TMD film using methods and materials known to those skilled in the art.

TMD sensors made in accordance with the methods of the invention are flexible, inexpensive, robust, and require only nanoamperes for operation, making them intrinsically ultra-low power, which are distinct advantages over other types of sensors. As physisorption is strongly dependent on the bandstructure of the material, a variety of TMDs can be combined into a single sensing suite to identify compounds of interest, analyze mixtures, and add sensitivity to the devices, building in essence a synthetic nose. (See U.S. Pat. No. 9,063,063, which is incorporated herein by reference.)

The methods of the invention include methods for detecting whether an unknown chemical vapor comprises a strong electron donor. The methods include providing at least one sensor comprising a transition metal chalcogenide thin film comprising at least one region having a 2H phase, and exposing the at least one sensor to an unknown chemical vapor. The transition metal chalcogenide thin film comprising at least one region having a 2H phase is then evaluated to determine whether the phase of the at least one region is 2H or 1T following exposure to the unknown chemical vapor. If the phase of the at least one region having a 2H phase has transitioned to the 1T phase, then the method has detected that the unknown chemical vapor comprises a strong electron donor. After detection has occurred, the results may be transmitted to provide information regarding the presence of the strong electron donor to one or more users.

The sensors of the invention use the 2H to 1T phase transition as either a concurrent or a stand-alone method for detecting and identifying chemical compounds of critical interest to the warfighter. The presence of a strong electron donor on an n-type TMD film induces a phase change from the 2H state, while the presence of a strong electron acceptor will cause a phase change from the 1T state. Likewise, for a p-type TMD film, modulation will occur in the 2H state for acceptor analytes and in the 1T state for donor analytes. As the amount of charge required to create a phase change in each TMD material is different (bandgaps for several TMDs, which are proportional to the energy required for a phase change: $MoS_2$=1.89 eV, $MoSe_2$=1.58 eV, $WS_2$=2.05 eV, $WSe_2$=1.61 eV), a suite of concurrently sensing TMD materials can allow electron donors/acceptors of varying strengths to be sensed and even identified with the necessary redundancy to minimize false alarms. Furthermore, the phase transition is reversible an unlimited number of times with spot annealing, the TMDs are inherently flexible, and they are inexpensive to produce. Therefore, sensors and systems of the invention provide a chemical vapor sensing ability that is ultra-low power, mechanically flexible yet robust, highly sensitive, highly selective, versatile, and inexpensive.

Another distinct advantage of TMD based sensors is the possibility of multi-modal vapor detection. This can be accomplished by monitoring the phase state of the material during and after chemical vapor exposure. As analytes donate charge to the TMD film, the film can undergo a phase change from the 2H to 1T state. FIG. 5A shows an $MoSe_2$ device. FIG. 5B shows the conductance of the device as a function of integrated exposure to butyl amine. After a certain amount of exposure, the conductance abruptly and terminally increases by at least two orders of magnitude and remains stable in that conductance state until annealed. Furthermore, the chemiresistive response of the devices recorded during exposure was observed to saturate after the above exposures, as shown in FIG. 5C. Above an exposure threshold, no response was observed, shown in the lower line (bottom axis). This behavior is consistent with a transition from a semiconducting to a metallic state, where added charge from adsorbates would have little to no effect and a charged adsorbate would be quickly screened and neutralized before eventually desorbing in regions that transitioned to the metallic state. The response recovers after a 400° C. anneal (shown in FIG. 5C, upper line, top axis), indicating a transition back to the 2H phase.

In addition to electrical characteristics, the phase change can be monitored optically, as shown in FIGS. 6A-6C and 8. Local phase changes result in a quenching of the PL and the shifting of emission from the neutral exciton to the charged exciton until the PL is completely quenched. In addition, Raman spectroscopy shows a decrease in amplitude and widening of the $E^1_{2g}$ and $A_{1g}$ modes along with the appearance of the J1, J2, and J3 modes expected for 1T phase material (see FIGS. 2B and 3B). Given both the electrical and optical responses of analytes, unique phase and electronic-based fingerprints of each analyte can be discerned, thus providing a multi-modal system for detection of TICs, CWAs, and chemicals related to explosives. More than one technique or method for determining the phase of the TMD film may be used concurrently for more accurate phase identification.

In accordance with the methods of the invention, the sensors used in the systems for detection may be calibrated by exposure to donor and acceptor analytes in a variety of humidities and temperatures, where PL and Raman spectroscopy analysis may be carried out to analyze the phase state of the film. The optoelectronic fingerprints of a variety of TICs, CWA simulants, and chemicals related to explosives (e.g. ammonia, DMMP, acetone, etc.) may be predetermined by testing in order to permit rapid identification of analytes in the field. Using a redundant T'd sensor (i.e., a flame ionization detector), the signal kinetics of the TMD device may be determined for different chemical challenges.

EXAMPLES

The invention will now be particularly described by way of example. However, it will be apparent to one skilled in the art that the specific details are not required in order to practice the invention. The following descriptions of specific embodiments of the present invention are presented for purposes of illustration and description. They are not intended to be exhaustive of or to limit the invention to the precise forms disclosed. Many modifications and variations are possible in view of the above teachings. The embodiments are shown and described in order to best explain the principles of the invention and its practical applications, to thereby enable others skilled in the art to best utilize the invention and various embodiments with various modifications as are suited to the particular use contemplated.

Example 1

Figure 2A:
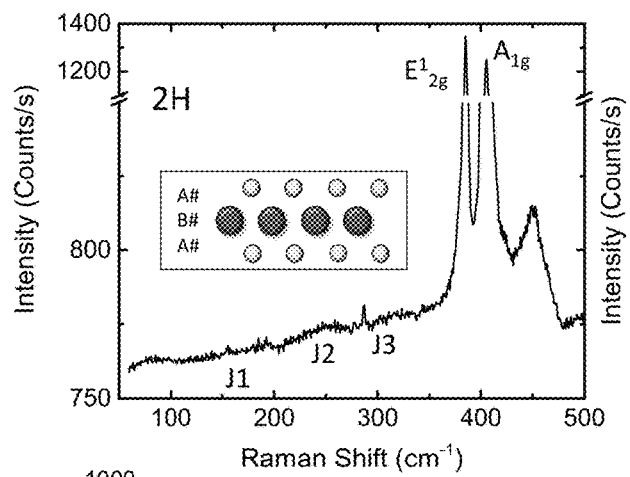
FIG. 2A is a graph showing a Raman spectroscopy spectrum with 488 nm laser showing a $MoS_2$ monolayer film in the 2H state.
Figure 2B:
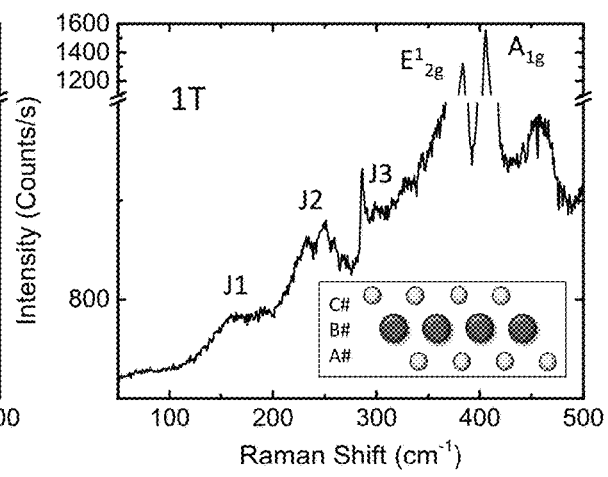
FIG. 2B is a graph showing a Raman spectroscopy spectrum with 488 nm laser showing a $MoS_2$ film in the 1T states after treatment with n-butyl lithium, where the emergence of the J1, J2, and J3 peaks indicates a successful transition.

$MoS_2$ flakes were mechanically exfoliated from a bulk crystal onto 275 nm $SiO_2/n^+$ Si. Thin layers were first visually identified with an optical microscope and then confirmed to be monolayer through Raman spectroscopy, as shown in FIGS. 2A and 2B, and photoluminescence spectroscopy (PL), shown in FIG. 2C. For Raman spectroscopy, the peak-to-peak separation of the $E^1_{2g}$ and $A_{1g}$ modes was associated with the number of layers, with a distance of ~18 $cm^{-1}$ being attributed monolayers and ~21.5 $cm^{-1}$ for bilayers (C. Lee, et al., "Anomalous lattice vibrations of single- and few-layer $MoS_2$," *ACS Nano* 4:2695 (2010)). For PL, because of the direct-to-indirect bandgap transition, a strong emission peak due to the A-exciton dominates for monolayers (A. Splendiani, et al., "Emerging photoluminescence in monolayer $MoS_2$," *Nano Lett.* 10:1271-1275 (2010)). As the number of layers increases, the intensity of the peak decreases rapidly and the position shifts to lower energy because of the drastic change in band structure. Therefore, in order to utilize photoluminescence spectroscopy determine the phase state of the $MoS_2$ film, the film is preferably monolayer or bilayer.

In order to identify the optical properties of the 1T vs. the 2H phase state, a film was transitioned from 2H to 1T by placing it in a n-butyl lithium (nbl) bath, which is known to successfully cause a phase change (G. Eda, et al., "Coherent atomic electronic heterostructures of single-layer $MoS_2$," *ACS Nano* 6:711 (2012); D. Voiry, et al., "Covalent functionalization of monolayered transition metal dichalcogenides by phase engineering," *Nat. Chem.* 7:45 (2015); and R. Kappera, et al., "Phase-engineered low-resistance contacts for ultrathin $MoS_2$ transistors, *Nat. Mater.* 13:1128 (2014).) FIGS. 2A and 2B display Raman spectra of the 2H (taken before nbl treatment) and 1T (taken after nbl treatment on the same sample) $MoS_2$ phases, respectively. The 2H phase had sharp $E^1_{2g}$ and $A_{1g}$ peaks, whereas the J1, J2, and J3 peaks (placed at 156, 226, and 333 $cm^{-1}$, respectively) (S. Jimenez Sandoval, et al., "Raman study and lattice dynamics of single layers of $MoS_2$," *Phys. Rev. B* 44:3955 (1991)) were difficult to discern from the noise, but hints of them were still visible. After treatment in nbl, the 1T phase $MoS_2$ sample had easily distinguishable J1, J2, and J3 peaks. The intensities of the $E^1_{2g}$ and $A_{1g}$ peaks had not changed significantly, but both had broadened slightly. The sharp peak at ~290 $cm^{-1}$ on both plots was attributed to the $MoS_2$ $E_{1g}$ mode (S. Jimenez Sandoval, et al., "Raman study and lattice dynamics of single layers of $MoS_2$," *Phys. Rev. B* 44:3955 (1991)). The enhanced visibility of the J1, J2, and J3 peaks taken together with the broadening of the $E^1_{2g}$ and $A_{1g}$ peaks were firm indicators of 1T phase material (D. Voiry, et al., "Phase engineering of transition metal dichalcogenides," *Chem. Soc. Rev.* 44, 2702 (2015); and S. Jimenez Sandoval, et al., "Raman study and lattice dynamics of single layers of $MoS_2$," *Phys. Rev. B* 44:3955 (1991)).

Figure 2C:
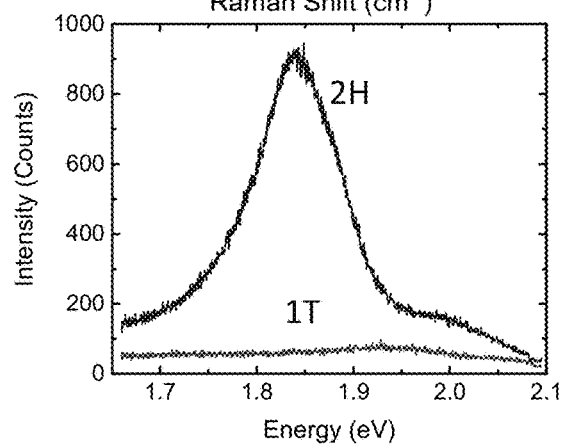
FIG. 2C is a graph of the results of photoluminescence spectroscopy of an as-exfoliated 2H $MoS_2$ film, showing a strong response indicative of a direct gap semiconductor.
Figure 2D:
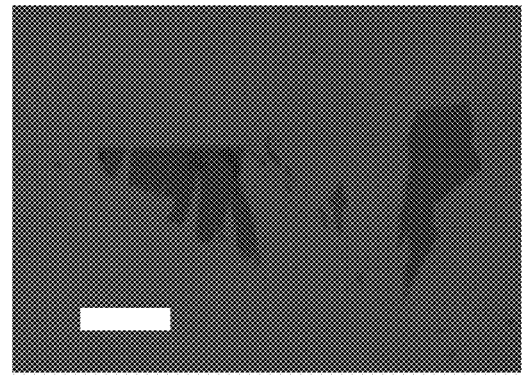
FIG. 2D is an optical microscopy image of a typical film used in this study, where the scale bar is 20 m.

Further phase identification can be found in the photoluminescence spectra, displayed in FIG. 2C. The 2H phase showed strong luminescence, as described above. After treatment with nbl and transition to the 1T metallic phase, the luminescence disappeared, as expected. The 2H phase can be recovered by annealing to ~400° C.

Example 2

Figure 3A:
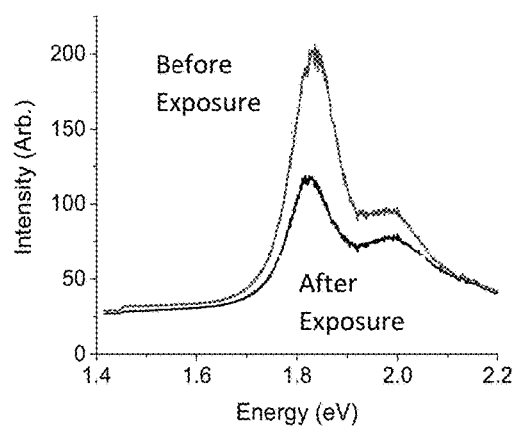
FIG. 3A is a graph showing photoluminescence spectroscopy spectra before (upper line) and after (lower line) exposure to chemical vapors from the strong electron donor tri-propyl amine (TPA).
Figure 3B:
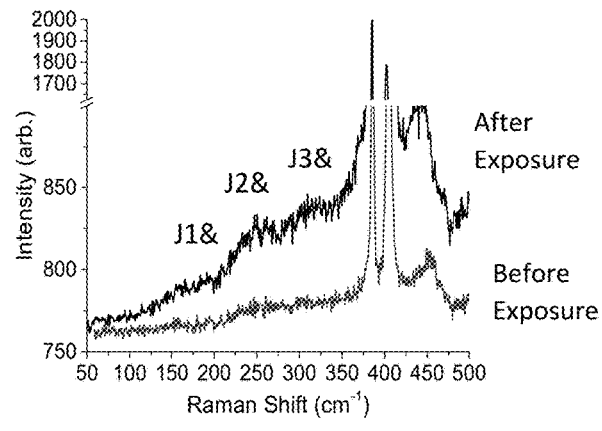
FIG. 3B is a graph showing Raman spectra taken before (lower line) and after (upper line) exposure to chemical vapors from a strong electron donor (TPA).

After the identification of $MoS_2$ flakes suitable for optical-based chemical vapor sensing, before-exposure PL and Raman scans were obtained, shown for a typical sample in FIGS. 3A and 3B, respectively. The films were then exposed to a strong electron donor vapor (in this case, tripropyl amine, or TPA). After exposure, the PL and Raman scans were re-taken, as shown in FIGS. 3A and 3B. The PL and Raman spectra of the material can be compared after exposure to the 1T state scans taken in FIG. 2B. A sharp decrease in PL intensity was observed, indicative of the 1T state. The appearance of the Raman J1, J2, and J2 peaks was observed, coupled with a wider $E^1_{2g}$ peak, also indicative of the 1T state. Therefore, it could be concluded that the $MoS_2$ film had at least partially transitioned to the 1T state due to exposure to a strong electron donor vapor. For sensor applications, a film can be exposed to an unknown analyte. If the PL and Raman after exposure indicates a phase change, then the sensor has tested positive for a strong electron donor.

Further identification of chemical vapors using the 2H to 1T phase transition can be accomplished using electric methods. Here, the $MoS_2$ films were processed into simple field effect transistor (FET) devices. Here, electron-beam lithography using PMMA resist followed by electron-beam evaporation of Ti/Au (5 nm/35 nm) and lift-off in acetone forms electrical contacts to the film (technique described in A. L. Friedman, et al., "Chemical vapor sensing to two-dimensional $MoS_2$ field effect transistor devices," *Sol. St. Elec.* 101:2-7 (2014)).

Example 3

The film formed in Example 2 was exposed to the strong electron donor triethylamine (TEA) while passing a voltage through the sample and monitoring the device's resistance. In the beginning, the sample showed a response to pulses of analyte, as shown in the top line of FIG. 4B and discussed in the literature (F. K. Perkins, et al., "Chemical vapor sensing with monolayer $MoS_2$," *Nano Lett.* 13:668-673 (2013); and A. L. Friedman, et al., "Chemical vapor sensing to two-dimensional $MoS_2$ field effect transistor devices," *Sol. St. Elec.* 101:2-7 (2014)). However, after a short period of time, without cleaning the sample, the electrical response saturated. This is shown in the middle line of FIG. 4B. Finally, the resistance dropped and the sample no longer responded to the analyte pulses, as shown in the lower line of FIG. 4B. The unresponsiveness to electron donors and the drop in resistance firmly supports the conclusion that the device had transitioned to the 1T state. The slow increase in resistance for all three curves shown in FIG. 4B was due to electrostatic charging in the constant nitrogen flow that was used to deliver the analyte, and can be discharged to recover the initial resistance state.

Example 4

Films of $MoSe_2$ and $MoS_2$ were mechanically exfoliated from bulk crystals and deposited on 275 nm thermally grown $SiO_2$ on $n^+$ Si substrates. Monolayer films were identified using optical contrast in a metallurgical compound microscope and confirmed using micro-spot (~1 m) PL and Raman spectroscopy. The PL and the Raman spectroscopies were performed using 532 nm and 488 nm excitations, respectively, both in ambient conditions. Less than 50 pW power with the 532 laser and less than 10 µW from the 488 laser was used in order to prevent damage to the films caused by local heating or other spurious effects. Using Raman spectroscopy, the $MoS_2$ monolayer thickness was confirmed by measuring a separation of 18.1 $cm^{-1}$ between the $A_{1g}$ and $E_{12g}$ mode peaks. The $MoSe_2$ monolayer was identified by an inactive $B_{2g}$ mode (expected at ~353 $cm^{-1}$) that is observable in few-layer films due to a loss of translation symmetry but absent in monolayers. Monolayer thickness was further confirmed by observation of the strong PL peak due to the A-exciton emission characteristic of the direct bandgap at monolayer thickness for both TMD films. Emission significantly decreases for the indirect gap bilayer film, and then almost completely vanishes for even thicker films.

Example 5

Chemical vapor exposure was performed using two different methods for either active or passive exposure monitoring. Active sample monitoring was accomplished electrically in a chemical vapor sensing apparatus. Devices were fabricated with Ti/Au (5 nm/35 nm) electrical contacts defined using electron-beam lithography in PMMA followed by electron-beam evaporation and lift-off in acetone. The $n^+$ Si substrate was used to provide a back gate electrode. Optical images of a monolayer $MoSe_2$ film before and after processing into a completed device are shown in FIG. 5A. Devices were then contacted with probes attached to computer-controlled lock-in amplifiers, either a low-impedance voltage source $V_s$=0 $V_{dc}$+0.1 $V_{ac,rms}$ with frequency on the order of 2 kHz, or a high impedance (1 MΩ) bias resistor Rb in parallel with the 10 MΩ input impedance of a lock-in amplifier, where the lock-in amplifier measures the frequency-matched voltage drop across the resistor. In this way, small voltage changes ΔV across Rb corresponding to small changes in differential conductivity $(G-G_0)/G_0$ were measured. The devices were placed on a sample chuck with heating capabilities for in situ device annealing, with the temperature being monitored by a thermocouple contacting the top face of the substrate. Heating the sample during measurements enabled the devices to recover more quickly after chemical vapor dosing. Devices were constantly under ac source-drain bias and 20 $V_{dc}$ gate-source bias while the films were intermittently exposed to vapors of butylamine (BuAm) or triethylamine (TEA), both strong electron donors, diluted under computer control into a flowing (51 pm) dry high purity $N_2$ ambient. $MoS_2$ sensor devices have high selectivity for strong electron donor compounds due to physisorption caused by charge transfer into the film. As expected, given the similar electronic and crystalline structures, $MoSe_2$ behaves similarly.

Example 6

FIG. 5B shows the normalized conductance of a $MoSe_2$ device taken during a series of intermittent analyte exposures performed over four days and measured in Langmuirs. Although this unit is more typically associated with studies performed under ultra-high vacuum (UHV) conditions, it is possible to assume that the $N_2$ ambient does not interact chemically with the surface of the film. Throughout the experiment, pure $N_2$ gas (except for the addition of dilute analyte) was flowing over the substrate, the substrate was heated to about 40° C., and the device was illuminated by white light. Exposures to BuAm or TEA ranged between concentrations of $1.4 \times 10^3$ to $2.8 \times 10^5$ ppm, over durations between 30 and 300 seconds. Intervals between exposures varied from 300 seconds to 18 hours. No significant change in conductivity was observed until about $4 \times 10^7$ Langmuirs integrated exposure, followed by an increase described well by a power law tending to saturation, until about $9 \times 10^8$ Langmuirs and an abrupt and essentially terminal increase of approximately two orders of magnitude higher conductance. At this time, the dip in normalized conductance observed at $\sim 2 \times 10^7$ Langmuirs cannot be explained, but it is theorized that this could be due to stochastic effects. Theoretical calculations and TEM measurements have determined that local strain (here provided by charge donation) can produce mixed phase films. Therefore, it is likely that a phase change is occurring in the vicinity of the adsorbed analytes where charge transfer is locally transitioning the lattice with increasing coverage and doping.

For one device, the as-fabricated device conductance was measured to be $\sim 1.4$ µS. This value is typical of $MoSe_2$ devices, especially those with Schottky contacts. At the end of the exposure experiments, the device conductance was measured to be $\sim 500$ µS. In general, the conductivity increase was approximately 1.5 to 2 orders of magnitude. This conductivity increase is consistent with a 2H-1T, phase transition. Further exposure to BuAm or TEA did not lead to a further evolution of conductivity, nor did annealing for five days at 55° C. in flowing $N_2$ under the measurement conditions described above, nor seven days at 28° C. on the shelf. Furthermore, the chemiresistive response of the devices recorded during exposure was observed to vanish after the above exposures, as shown in FIG. 5C. In this curve, the middle line (bottom axis) shows the conductance response of the device to a series of pulsed 0.04% $P_0$ BuAm exposures. After a certain exposure threshold, no response was observed, shown in the lower line (bottom axis). This behavior is consistent with a transition from a semiconducting to a metallic state, where added charge from adsorbates would have little to no effect and a charged adsorbate would be quickly screened and neutralized before eventually desorbing in regions that transitioned to the metallic state. Although a highly doped $MoSe_2$ device would display greatly increased conductivity and a smaller response to pulsed vapors, it would not show an abrupt and terminal change in conductivity and the complete cessation of response to pulsed analyte vapors. At this point, this device was annealed in vacuum. The device response did not recover until annealed at 400° C. for 2 hours, with lower temperature vacuum annealing failing to result in recovery. The initial conductance was essentially recovered by the 400° C. anneal, as well as a chemiresistive response (shown in FIG. 5C, upper line, top axis), indicating a likely transition back to the 2H phase.

A possible source of the observed decrease in resistance could be additional or continuing surface doping from the analyte. Indeed, previous research shows that significantly lower resistances and orders of magnitude higher carrier concentrations are found in $MoS_2$ films contacted by surface-stabilized, amine-based polymer films formed by liquid chemistry methods, and hence continuously doped. When the amine-based film is removed from the $MoS_2$ by annealing, the initial properties recover. However, density functional theory (DFT) analysis of adsorption on $MoS_2$ films predicts that most molecules only weakly physisorb to the surface of the film and will spontaneously desorb under ambient conditions. Exceptions include sulfur-containing thiols and certain oxygen-containing species, none of which were used in this Example, that can both physisorb to the surface of the film and chemisorb at defect sites. Nonetheless, thermal desorption spectroscopy studies demonstrated that even these more deeply-bound molecules will spontaneously desorb well below room temperature. More importantly, these studies concluded that volatile organic compounds and $NH_3$, which are chemically very similar to the analytes used here, only very weakly physisorb to the surface with adsorption energies in the range of 10-200 meV, depending on details of the adsorption site chemistry and the DFT model used. This is on order of kT ($\sim 25$ meV) for the sensing conditions of this Example. Thus, simple persistent doping is unlikely because the analyte molecules are known to desorb from the film quickly under the conditions used in this Example. Moreover, no change in conductance or optical behavior was observed after placing the sample in vacuum or vacuum annealing at temperatures below the likely transition temperature ($\sim 400°$ C.), after which it is even more unlikely that even the most strongly adsorbed dopant will remain adsorbed. Therefore, the conclusion is that doping effects are not causing the observed behavior.

Example 7

FIG. 5D shows current vs. back gate voltage at a constant 1 V source-drain bias for a device before exposure, after terminal exposure, and after annealing in vacuum at 400° C. If a device is increasingly doped until the film changes phase in its entirety, an upwards shift in conductance would be expected with each successive exposure, until finally a flat line is observed at high conductance. However, a partial phase change creates a film that has metallic islands or ribbons imbedded in a semiconductor. Similar hybrid semiconductor-metal structures have been studied in the past and found to behave differently than the picture expected for increasing doping. For example, some experiments have demonstrated a shifting between multiple conduction mechanisms including tunneling, variable range hopping, and thermally activated regimes that are all affected by bias and electric field. Such a mixed semiconductor-metal material FET can result in an anomalously large electroconductance, governed by the size of the metallic islands. The metallic areas act as current shunts in zero electric field, with most of the current flowing through them. In an applied electric field, there are more current paths around the metallic regions as the resistivity of the semiconductor in this region is reduced. In other words, electrons will take the path of least resistance, which in the off state of the FET would be some form of percolative motion through the metallic islands. However, when the gate is turned on, drastically lowering the resistance of the surrounding semiconducting regions, parallel conductance through both metallic and semiconducting regions becomes much more likely. This makes it easier to gate modulate the device after the partial phase change, similar to what is shown in FIG. 5D. These data are in strong agreement with the partial phase transition hypothesis, but not in agreement with the doping hypothesis.

Example 8

In FIG. 10A, IV curves for an as-fabricated MoSe2 device are presented, the same device after a saturation dose of TEA, and after a 2-hour vacuum anneal at 400° C. A semi-log scale is used to make comparison easier. It is important to note that large double Schottky barriers necessitate using a higher bias voltage to reach the linear portion of the curve. The resistance of the as-fabricated device is ~25 GΩ, while the dosed device (partially transitioned) has a resistance of ~228 MΩ, a change of approximately 2 orders of magnitude.

In FIG. 10B shows the current vs. (wider) gate voltage for as fabricated, TEA exposed, and vacuum annealed device. The exposed, partially transitioned device turns on much faster and has conductance behavior comparable to other semiconductor channel devices with metallic inclusions, as discussed in the main text.

Example 9

Active electrical measurements were performed on $MoS_2$ FET devices using the home-built chemical vapor sensing apparatus and methods. All devices responded to TEA, resulting in the observation of behavior similar to the $MoSe_2$ FET devices.

After a series of pulse sequences, the device response degrades and eventually stops. Initial resistance at a back gate voltage of 10 V was ~1 MΩ. The resistance decreased to ~18 kΩ after a number of TEA pulsed sequence exposures. Subsequent pulse sequences show unresponsive devices that must be annealed to recover functionality.

Pulsed analyte vapor response curves similar to that in FIG. 5C were observed in previous studies and were described with a model that included two recovery components after the analyte flow was switched off. In the first component, the weakest of the physisorbed molecules desorb, resulting in a rapid decrease in conductivity (the "fast recovery"). Then, the more strongly adsorbed molecules desorb over a longer time, resulting in a slower decrease in conductivity until the sample has recovered, noted by a flat conductance line (the "slow recovery"). The timescale of this total process is on order of hundreds of seconds. This type of behavior is not observed in TMD sensors exposed to stronger bonding thiols or oxygen species. With these types of dopants, there is no recovery or cessation of analyte responsive conductance modulation. If the adsorption was mostly due to bonding at defect sites, it is expected a similar behavior would result, but this is clearly not what has been observed. This is most likely because once the chemisorption binding sites are saturated, these compounds can still actively physisorb/desorb at weaker binding sites. This is further evidence that doping by persistent adsorbed analytes is not the cause of the observed behavior.

Example 10

Further corroborating evidence of a chemically-induced phase transition can be gleaned from passive optical measurements of analyte-exposed films. In these experiments, no electrical signals were applied, and the substrate was at room temperature (25° C.) and in darkness. Here, as-exfoliated $MoX_2$ films are placed in a small (100 mL) sealed bell jar containing an open vial of tripropylamine (TPA), another strong electron donor. This analyte was chosen for these experiments because of its lower vapor pressure ($P_{0, TPA}$=2.2×103 ppm as compared to $P_{0,BuAm}$=1.4×105 ppm, $P_{0,TEA}$=7.1×104 ppm), thus making it possible to generate vapor and expose the film without a directed flow. Moreover, the analyte spontaneously and immediately desorbs when the film is removed from the bell jar, as discussed above, but at a rate commensurate with a relatively low vapor pressure. The films were periodically removed from the bell jar for PL and Raman measurements and were replaced in the bell jar for further vapor exposure.

FIG. 6A shows Raman spectra from the monolayer $MoSe_2$ film shown in the inset after a series of exposures to TPA for 0.5, 2.5, 6.5, and 10 days, corresponding respectively to cumulative exposures of 72, 360, 940, and 1400× $10^9$ Langmuirs. The black dot in the inset image shows the position at which the presented spectra were measured. There are a variety of features in these spectra including sharp peaks at the $A_{1g}$ (241 $cm^{-1}$) and $E_{12g}$ (287 $cm^{-1}$) energies, as well as a series of broad peaks from second order Raman processes, which are not labeled. No obvious changes in the Raman spectrum were induced by analyte exposure. Secondary interactions or a breakdown of local symmetry, such as caused by a phase change, could possibly lead to the formation of new broad peaks in the spectrum. While it is still possible that there are additional peaks in this data, any new features are well within the noise of the measurement. There is believed to be no information in the literature on the Raman spectrum of 1T $MoSe_2$.

FIG. 6A shows a wider range plot than in the main paper showing the Raman scan from the point indicated on the $MoSe_2$ flake image by the black dot for a variety of exposures times and annealing temperatures. Raman maps of the entire film were acquired. The images on the right in FIG. 6A show the integrated intensity of the A1g and E12g peaks over the entirety of the film. The intensity plots are superimposed over optical images. The Raman spectra were quite uniform over this area.

FIG. 11A (left plot) shows the same data as FIG. 6A, plotted on a log scale. There are no additional peaks to be found that are greater than the noise. The panels on the right (FIGS. 11B-11C) plot the peak positions (FIG. 11B) and the peak power (FIG. 11C) of the $A_{1g}$ and $E_{12g}$ peaks as a function of exposure or annealing event. Previous studies have shown that strain is associated with a significant amount of Raman peak mobility. No significant peak mobility are observed in this data.

After 10 days of TPA exposure, the sample was annealed in vacuum at 300° C., 400° C., and 500° C. for 2 hours each time, taking measurements between each annealing step. No measurable change compared to the initial state of the film was observed.

FIGS. 6B and 6C show Raman spectroscopy data from the monolayer $MoS_2$ film shown in the inset. FIG. 6B shows the Raman data from an as-deposited 2H phase film and FIG. 6C shows the Raman data collected after the film was exposed to TPA for 7 days (1×$10^{12}$ Langmuirs). After exposure, the J1 (156 $cm^{-1}$), J2 (226 $cm^{-1}$), and J3 (300 $cm^{-1}$) mode peaks were weakly visible, but still easily discernable. These peaks are expected for the 1T phase due to superlattice distortions but are absent in the 2H phase. Where a 2H-1T phase change was initiated with an aqueous n-butyl lithium treatment, the J1, J2 and J3 peaks were also observed with a similar width, but with greater relative intensity. In a fully metallic phase film, these peaks are at slightly different positions and even greater in relative intensity. However, when the 2H and 1T phase coexist in the same film, there are weak J1, J2, and J3 peaks, suggesting support for a partial transition to the 1T phase, consistent with the electrical measurement results. After annealing at 400° C. in vacuum for 2 hours, the film recovered to the 2H-like state.

Figure 7A:
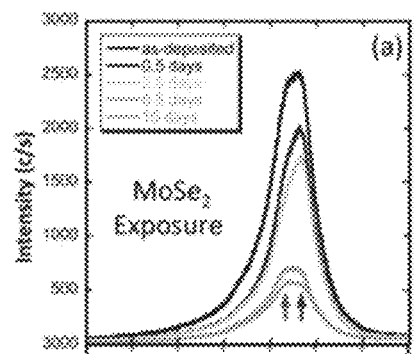
FIG. 7A is a photoluminescence (PL) spectra of a monolayer $MoSe_2$ film shown in FIG. 6A after a series of exposures to TPA in a bell jar, as indicated. The left and right arrows indicate the trion and neutral exciton, respectively. The as-deposited film lost 80% of its intensity after 10 days of exposure, indicating a partial transition to the 1T phase.
Figure 7C:
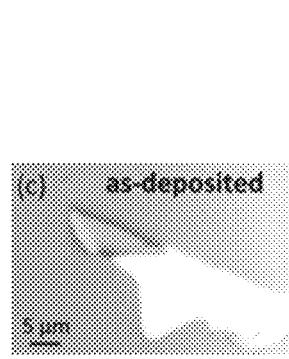
FIGS. 7C-7E are PL peak intensity maps superimposed onto the optical image of the $MoSe_2$ film showing both the decrease of intensity/recovering of the film and the uniformity of the emission.

FIG. 7A shows PL spectra taken concurrently with the Raman data shown in FIG. 6A from the passively-exposed $MoSe_2$ film. In these spectra, there are clearly two components. The higher energy component (blue arrow) is assigned to the neutral exciton and the lower energy component (red arrow) is assigned to the charged exciton, or trion. FIG. 7B shows PL spectra on the same $MoSe_2$ film after a series of vacuum annealing steps compared to the as-deposited and partially transitioned film, as indicated. It is evident that after a 400° C. vacuum anneal, the intensity has mostly recovered. In general, the oscillator strength of the trion is less than the neutral exciton for all $MX_2$ films. Therefore, it can be concluded that the recovery is likely complete. FIGS. 7C-7E show PL integrated intensity maps superimposed over the sample microscope image for FIG. 7C the as-deposited flake, FIG. 7D after 6.5 days exposure ($940 \times 10^9$ Langmuirs), and FIG. 7E after the 400° C. anneal, respectively.

Figure 7F:
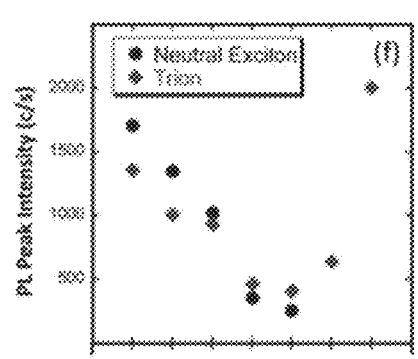
FIG. 7F shows PL peak intensity as a function of event, further elucidating the effect of TPA exposure and annealing.
Figure 7B:
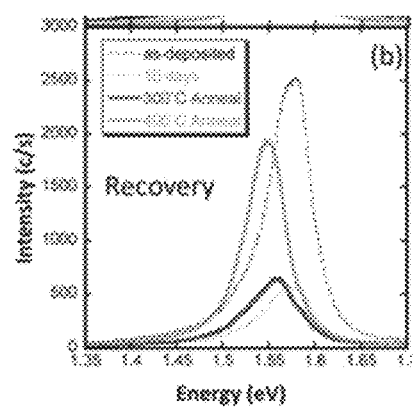
FIG. 7B is a PL spectra on the same $MoSe_2$ film after a series of annealing steps compared to the as-deposited and partially transitioned film, as indicated. After annealing at 400° C., the film recovered to within ~80% of the original intensity, indicating a transition back to the 2H phase.
Figure 7D:
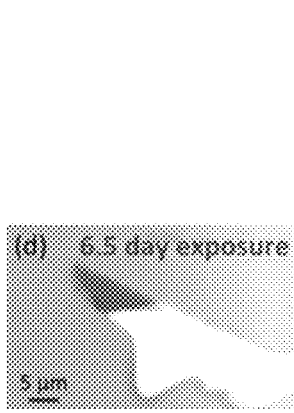
Figure 7G:
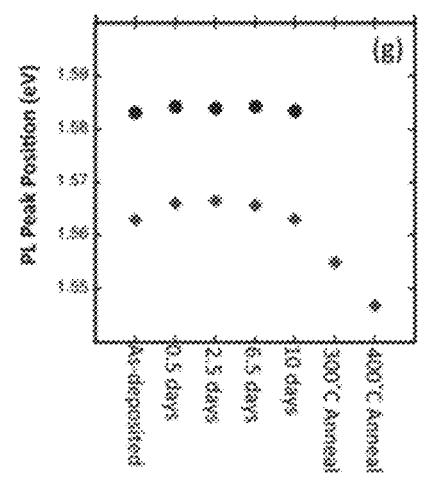
FIG. 7G shows the PL peak position of the two peaks indicated by the arrows in FIG. 7A as a function of exposure/annealing events.
Figure 7E:
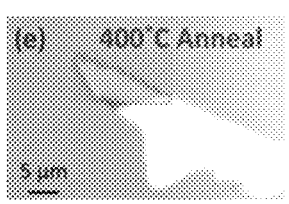

The evolution of the intensity of the PL emission from the neutral exciton (blue circles) and trion (red diamonds) as a function of exposure are detailed in FIG. 7F along with the peak position as a function of event (either exposure or annealing) in FIG. 7G. In these figures, the plotted intensities and positions were derived from the spectra in FIGS. 7A-7B. As the sample is exposed to TPA, the intensity of both components decreases steadily with a general shift in spectral weight from the neutral exciton to the trion. Eventually the trion intensity becomes the dominant emission channel. This behavior is consistent with the hypothesized model of a transition to the 1T phase. Doping could cause a similar reduction in PL intensity. However, very little if any analyte remains on the film while the PL spectra are taken. Because the film retains its lower intensity PL state after vacuum annealing at temperature below the likely transition temperature (~400° C.), where given the binding energies of adsorbates it is extremely unlikely that they persist, doping is not a probable cause of the observed behavior. The persistence of the trion peak indicates excess charge remains in the film. In a mixed phase material, the areas of the film that are 1T could be a source of this excess charge. The formation and dissolution of trions during the charge transfer process has been theoretically shown to result in changes to the sample mobility. This behavior is therefore also consistent with the increased conductance observed during the active measurements reported above.

Additionally, oxidation can be ruled out as a cause of the PL intensity decrease (and, consequently, as a cause of all of the exposure data presented here). As can be seen in FIGS. 7A-7G, the sample intensity recovered after annealing at 400° C. in vacuum for 2 hours, which is unlikely to be sufficient for thermal reduction. Moreover, as DFT calculations and other research confirms, oxygen species are charge acceptors, which would result in the suppression of the trion peak for our n-type samples, opposite of what is observed.

In FIG. 7G the peak position of the neutral exciton (blue circles) and trion (red diamonds) is plotted as a function of TPA exposure. The peak separation of ~20 meV is on the order of the trion binding energy reported elsewhere for $MoSe_2$. In addition to becoming the dominant emission channel, a peak shift in the trion as a function of exposure was observed. A peak shift during a phase transition was observed previously in $MoS_2$, and may be attributable to strain. While this seems to be a reasonable explanation given the intimate relationship between strain and the phase change, no significant change in the Raman peaks was observed. It is more likely that the shift in trion position is due to band gap renormalization associated with the increase in charge density in the film.

Figure 8:
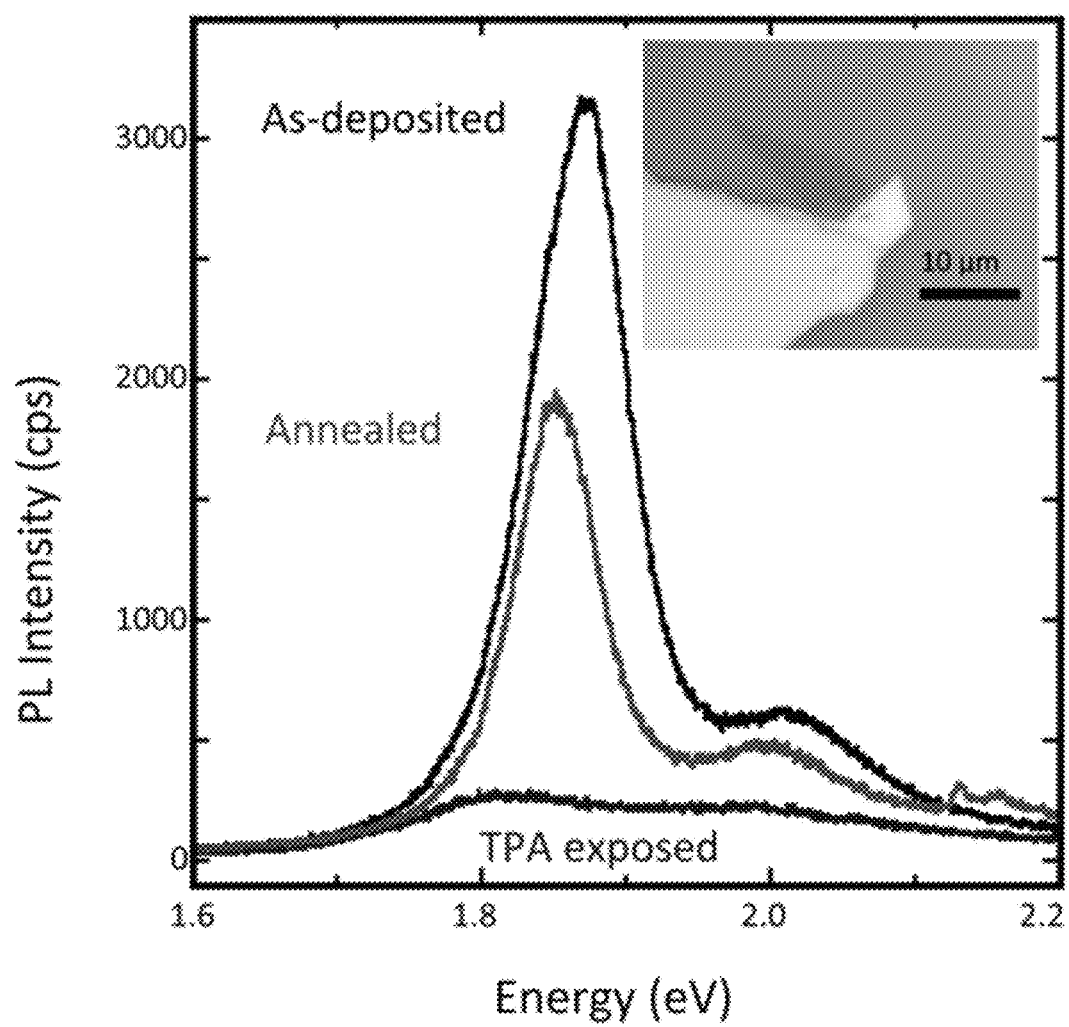
FIG. 8 is a PL spectra of a $MoS_2$ film for as-deposited (upper line) and after 10 days of exposure to TPA (lower line) and XPS performed in UHV. There was almost a full extinction in peak intensity and a ~10 meV redshift in energy, indicating a partial 2H-1T phase change. The middle peak corresponds to the PL after annealing for 2 hrs in vacuum at 450° C.

While the behavior present in FIGS. 7A-7G is for a specific $MoSe_2$ film, a similar pattern is observed in other samples as well. FIG. 8 shows PL spectra taken on a $MoS_2$ film exposed to TPA for 10 days. The upper line shows the as-deposited emission, while the lower line shows the emission after 10 days of exposure and after acquiring XPS data in UHV (discussed below). An almost complete quenching of emission was observed. The middle line shows the recovery of the emission after annealing in vacuum for 2 hrs. at 450° C. The $MoS_2$ film qualitatively behaves similarly in all respects to the $MoSe_2$ film. Based on the predicted lower phase transition energy of $MoSe_2$ vs. $MoS_2$, the transition is expected to occur with less exposure for $MoSe_2$, which does appear to be the case, at least qualitatively. It is interesting to note that the actively measured devices transitioned faster (estimated to be $5 \times 10^3$ times faster) than the passively measured films. It was shown theoretically that an electric field, such as applied by a back gate, could aid in the charge transfer process, which would cause a faster phase transition.

CONCLUSIONS

Electron-donors can impart charge to the surface of transition metal dichalcogenide (TMD) films while interacting with the film via a weak physisorption bond, making the films useful as vapor and gas sensors.

In the Examples, monolayer $MoS_2$ and $MoSe_2$ films were exposed to strong electron-donor chemical vapor analytes. Based on analysis of the resultant behavior and taking into consideration doping effects, exposure to strong electron-donors could be a method of inducing the semiconductor-metal 2H-1T TMD phase transition. The conductance response to strong electron donors in both monolayer $MoS_2$ and $MoSe_2$ FET devices ceases after moderate exposure, with final value of the conductance being on order of that expected for the 1T phase. Full device relaxation back to a semiconducting state is accomplished by annealing in vacuum at 400° C. Chemically-exposed TMD films were intermittently interrogated with Raman and photoluminescence spectroscopy. Weak characteristic 1T phase Raman features were observed for $MoS_2$, and quenching of the photoluminescence of both TMD films was observed, and was recoverable with annealing. These effects cannot be explained by doping alone, and the results suggest a mechanism for a new type of passive chemical vapor sensor.

When taken together, the transport, Raman, and PL data provide strong evidence that the $MoX_2$ films have substantially transitioned from the 2H phase to the 1T phase due solely to chemical vapor exposure. The hallmarks of this transition in the sensor devices of the invention is the change from a low conductance, actively sensing state to a high conductance, unresponsive state following extensive analyte exposure. The PL peak quenching and subsequent recovery in both $MoX_2$ films and the appearance of the 1T-phase $MoS_2$ J1, J2, and J3 Raman peaks further supports the conclusion of a phase change. It is unclear at this time whether the transition is localized to small islands in the film or includes domains across the majority of the film, although transport data supports the small islands hypothesis.

Detailed microscopy measurements such as transmission electron microscopy (TEM) can provide a direct method for visualizing the different phases. However, because the 2H and 1T phases have similar lattice constants and symmetries, and since monolayer samples have small TEM imaging cross sections, such measurements can be extremely challenging. Moreover, due to transferability and optical contrast considerations, the most commonly studied high-quality mechanically exfoliated films are not easily amenable to TEM studies. Thirdly, optical measurements can be used as differentiation methods because the photoluminescence (PL) readily observed from the semiconducting phase is quenched in the metallic phase. However, because multiple phases can exist in the same TMD film, one cannot expect a complete suppression of PL for a partially transitioned film, but at most a partial reduction in PL. Additionally, doping effects can also cause a reduction in PL, so other methods must be used concurrently for accurate phase identification.

Evidence for a chemical vapor induced 2H-1T phase change in monolayer $MoSe_2$ and $MoS_2$ films has been provided in these Examples. The conductance of TMD devices was actively monitored as a function of exposure to various analytes. In an ambient atmosphere intermittently containing dilute vapors of strong electron-donor analytes, there was both a significant increase in conductance as well as an attenuation of chemiresistance response after an observed cumulative exposure. The higher conductance state persisted even after all analyte had almost certainly desorbed from the film surface, and the samples recovered their original optical and electronic properties after annealing above the likely transition temperature. These behaviors support the conclusion of a vapor-induced partial phase change. Finally, to provide further corroborating evidence that the $MoX_2$ films undergo the phase transition, Raman and photoluminescence spectroscopy (PL) were used to characterize the films before and after exposure to strong electron donor analytes. The TMD $MoS_2$ in particular, when very thin, has been shown to exhibit additional Raman features (identified as J1, J2, and J3) when it transitions from 2H to 1T, but these peaks can be very weak and difficult to discern if both phases coexist. Moreover, recent studies show that most common methods of inducing a 2H to 1T transition leave as much as 20-50% of the film in the 2H phase, resulting in a variety of possible discrepancies in the literature as to the Raman behavior of a true 1T phase film.

By harnessing the phase transition to directly sense strong electron donor analytes, an entirely new chemical vapor sensing paradigm has been created by the sensors, systems, and methods of the invention, whereby passive-type optical measurements could be combined with or used separately from active conductance measurements for the identification of analyte vapors, all with the same device. As most chemical vapor analytes of interest (for instance, nerve gas and explosive by-products and constituents) are strong electron donors or acceptors, the 2H-1T phase transition can be used as the operating mechanism for a new method of identifying chemical compounds. The presence of a strong electron donor will cause a phase change in the 2H state, thus signaling the presence of a possibly dangerous vapor. As the amount of charge necessary to induce a phase change in each TMD material is different, a suite of concurrently-sensing TMD materials could allow various strength electron donors/acceptors to be sensed and even identified with the necessary redundancy to minimize error. Furthermore, the phase transition is infinitely cycle-able with annealing, and TMDs are inherently flexible and relatively inexpensive to produce.

It will, of course, be appreciated that the above description has been given by way of example only and that modifications in detail may be made within the scope of the present invention.

Throughout this application, various patents and publications have been cited. The disclosures of these patents and publications in their entireties are hereby incorporated by reference into this application, in order to more fully describe the state of the art to which this invention pertains.

The invention is capable of modification, alteration, and equivalents in form and function, as will occur to those ordinarily skilled in the pertinent arts having the benefit of this disclosure. While the present invention has been described with respect to what are presently considered the preferred embodiments, the invention is not so limited. To the contrary, the invention is intended to cover various modifications and equivalent arrangements included within the spirit and scope of the description provided above.

What is claimed:

1. A sensor for detecting strong electron donors, comprising:
    a substrate;
    a transition metal dichalcogenide thin film comprising at least one first region having a 2H phase, wherein the transition metal dichalcogenide thin film is on the substrate;
    at least two second regions of the transition metal dichalcogenide thin film; and
    at least two electrically-conductive leads, wherein the at least two second regions of the transition metal dichalcogenide thin film are directly in contact with the at least two electrically-conductive leads;
    wherein the at least two second regions of the transition metal dichalcogenide thin film that are directly in contact with the at least two electrically-conductive leads have a 1T phase.

2. The sensor of claim 1, further comprising a power source.

3. The sensor of claim 1, wherein the power source is selected from the group consisting of electrochemical cells, solar cells, fuel cells, and capacitors.

4. The sensor of claim 1, wherein the substrate comprises a material selected from the group consisting of silicon, silicon dioxide, aluminum oxide, sapphire, germanium, gallium arsenide, alloys of silicon and germanium, indium phosphide, polypropylene, polyethylene, polyethylene naphthalate, polyether ether ketone, polycarbonate, polyethersulfone, polyimide, and combinations thereof.

5. The sensor of claim 1, wherein the transition metal dichalcogenide thin film is selected from the group consisting of $MoS_2$, $MoSe_2$, $WS_2$, $WSe_2$, $NbS_2$, $NbSe_2$, $TaS_2$, and $TaSe_2$.

6. The sensor of claim 1, wherein the at least two electrically-conductive leads comprise materials selected from the group consisting of gold, titanium, chromium, platinum, palladium, copper, silver, aluminum, and alloys and combinations thereof.

7. The sensor of claim 1, further comprising an electromagnetic signal transmitter.

8. The sensor of claim 7, wherein the electromagnetic signal transmitter is a radio transmitter.

* * * * *